United States Patent
Jaeschke et al.

(10) Patent No.: US 8,648,088 B2
(45) Date of Patent: Feb. 11, 2014

(54) ETHYNYL NITROGEN CONTAINING HETEROARYL PYRAZOLIDIN-3-ONE DERIVATIVES

(75) Inventors: Georg Jaeschke, Basel (CH); Synese Jolidon, Blauen (CH); Lothar Lindemann, Basel (CH); Antonio Ricci, Birsfelden (CH); Daniel Rueher, Raedersdorf (FR); Heinz Stadler, Basel (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/454,167

(22) Filed: Apr. 24, 2012

(65) Prior Publication Data

US 2012/0277243 A1    Nov. 1, 2012

(30) Foreign Application Priority Data

Apr. 26, 2011   (EP) .................................. 11163708

(51) Int. Cl.
    *C07D 401/04*    (2006.01)
    *A61K 31/506*    (2006.01)
    *C07D 403/04*    (2006.01)
    *A61K 31/4439*    (2006.01)

(52) U.S. Cl.
    USPC .......... 514/275; 514/341; 544/331; 546/276.1

(58) Field of Classification Search
    USPC ................. 514/341, 275; 546/276.1; 544/331
    See application file for complete search history.

(56) References Cited

U.S. PATENT DOCUMENTS

2009/0042855 A1   2/2009   Conn et al.
2010/0179161 A1*  7/2010   Bandodkar et al. ...... 514/252.05

OTHER PUBLICATIONS (International Search Report PCT/EP2012/057336 Apr. 23, 20102).

* cited by examiner

*Primary Examiner* — James O Wilson
*Assistant Examiner* — Cecilia M Jaisle

(57) ABSTRACT

The present invention relates to ethynyl derivatives of formula I

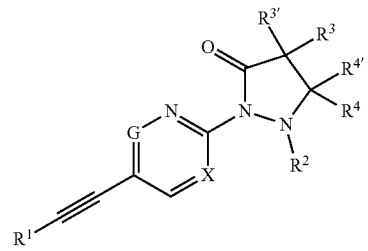

wherein G, X, $R^1$, $R^2$, $R^3$, $R^{3'}$, $R^4$, and $R^{4'}$ are as defined herein or to a pharmaceutically acceptable acid addition salt, to a racemic mixture, or to its corresponding enantiomer and/or optical isomer and/or stereoisomer thereof. Compounds of formula I are positive allosteric modulators (PAM) of the metabotropic glutamate receptor subtype 5 (mGluR5).

13 Claims, No Drawings

ETHYNYL NITROGEN CONTAINING HETEROARYL PYRAZOLIDIN-3-ONE DERIVATIVES

PRIORITY TO RELATED APPLICATION(S)

This application claims the benefit of European Patent Application No. 11163708.8, filed Apr. 26, 2011, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to site different from the highly conserved orthosteric binding site. Positive allosteric modulators of mGluR5 have emerged recently as novel pharmaceutical entities offering this attractive alternative. Positive allosteric modulators have been described, for example in WO2008/151184, WO2006/048771, WO2006/129199 and WO2005/044797 and in *Molecular Pharmacology*, 40, 333-336, 1991; *The Journal of Pharmacology and Experimental Therapeutics*, Vol 313, No. 1, 199-206, 2005;

Positive allosteric modulators are compounds that do not directly activate receptors by themselves, but markedly potentiate agonist-stimulated responses, increase potency and maximum of efficacy. The binding of these compounds increase the affinity of a glutamate-site agonist at its extracellular N-terminal binding site. Positive allosteric modulation is thus an attractive mechanism for enhancing appropriate physiological receptor activation. There is a scarcity of selective positive allosteric modulators for the mGluR5 receptor. Conventional mGluR5 receptor modulators typically lack satisfactory aqueous solubility and exhibit poor oral bioavailability. Therefore, there remains a need for compounds that overcome these deficiencies and that effectively provide selective positive allosteric modulators for the mGluR5 receptor.

SUMMARY OF THE INVENTION

The present invention provides compounds of formula I and their pharmaceutically acceptable salts, pharmaceutical compositions containing them, processes for their production, and their use in the treatment or prevention of disorders relating to positive allosteric modulators for the mGluR5 receptor, such as schizophrenia, tuberous sclerosis, and cognition.

The present invention provides ethynyl derivatives of formula I

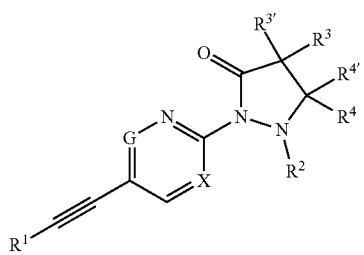

wherein
X is N or CH;
G is N or CH;
with the proviso that only one of X or G can be nitrogen;
$R^1$ is phenyl or pyridyl, each of which is optionally substituted by halogen, lower alkyl or lower alkoxy;
$R^2$ is hydrogen or lower alkyl or together with $R^4$ form a $C_3$-$C_6$-cycloalkyl;
$R^3/R^{3'}/R^4/R^{4'}$ are each independently hydrogen, lower alkyl or $CF_3$;
or a pharmaceutically acceptable acid addition salt, a racemic mixture, or its corresponding enantiomer and/or optical isomer and/or stereoisomer thereof.

Compounds of formula I are positive allosteric modulators (PAM) of the metabotropic glutamate receptor subtype 5 (mGluR5).

Compounds of formula I are distinguished by having valuable therapeutic properties. They can be used in the treatment or prevention of disorders, relating to positive allosteric modulators for the mGluR5 receptor.

The most preferred indications for compounds which are positive allosteric modulators are schizophrenia and cognition.

DETAILED DESCRIPTION OF THE INVENTION

The following definitions of the terms used in the present description apply irrespective of whether the terms in question appear alone or in combination.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "alkoxy" denotes a group —O—R' wherein R' is lower alkyl as defined above.

The term "halogen" denotes fluoro, chloro, bromo or iodo.

The term "$C_3$-$C_6$-cycloalkyl" denotes a monovalent saturated monocyclic or bicyclic hydrocarbon group of 3 to 6 ring carbon atoms. Particular cycloalkyl groups are cyclopropyl, cyclobutanyl, cyclopentyl, and cyclohexyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient," "therapeutically inert excipient" and "pharmaceutically acceptable carrier" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

One embodiment of the invention provides compounds of formula IA

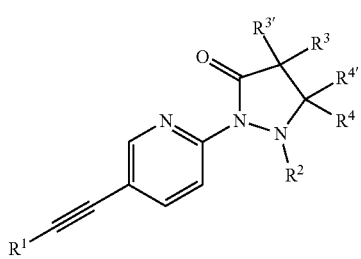

IA wherein
$R^1$ is phenyl or pyridyl, each of which is optionally substituted by halogen, lower alkyl or lower alkoxy;
$R^2$ is hydrogen or lower alkyl or together with $R^4$ form a $C_3$-$C_6$-cycloalkyl;
$R^3/R^{3'}/R^4/R^{4'}$ are each independently hydrogen, lower alkyl or $CF_3$;
or a pharmaceutically acceptable acid addition salt, a racemic mixture, or its corresponding enantiomer and/or optical isomer and/or stereoisomer thereof,
for example the following compounds
5,5-dimethyl-2-(5-phenylethynyl-pyridin-2-yl)-pyrazolidin-3-one;
(RS)-5-isopropyl-2-(5-phenylethynyl-pyridin-2-yl)-pyrazolidin-3-one;
1,5,5-trimethyl-2-(5-phenylethynyl-pyridin-2-yl)-pyrazolidin-3-one;
1,5,5-trimethyl-2-(5-m-tolylethynyl-pyridin-2-yl)-pyrazolidin-3-one;
2-[5-(3-fluoro-phenylethynyl)-pyridin-2-yl]-5,5-dimethyl-pyrazolidin-3-one;
2-[5-(3-fluoro-phenylethynyl)-pyridin-2-yl]-1,5,5-trimethyl-pyrazolidin-3-one;
2-[5-(3-chloro-phenylethynyl)-pyridin-2-yl]-1,5,5-trimethyl-pyrazolidin-3-one;
2-[5-(4-fluoro-phenylethynyl)-pyridin-2-yl]-5,5-dimethyl-pyrazolidin-3-one;
(RS)-1-(5-phenylethynyl-pyridin-2-yl)-tetrahydro-pyrrolo[1,2-b]pyrazol-2-one;
2-[5-(2-chloro-pyridin-4-ylethynyl)-pyridin-2-yl]-1,5,5-trimethyl-pyrazolidin-3-one;
2-[5-(2,5-difluoro-phenylethynyl)-pyridin-2-yl]-5,5-dimethyl-pyrazolidin-3-one;
1-ethyl-5,5-dimethyl-2-(5-phenylethynyl-pyridin-2-yl)-pyrazolidin-3-one;
1-ethyl-2-[5-(4-fluoro-phenylethynyl)-pyridin-2-yl]-5,5-dimethyl-pyrazolidin-3-one;
(RS)-1-ethyl-5-isopropyl-2-(5-phenylethynyl-pyridin-2-yl)-pyrazolidin-3-one and
(RS)-5-Methyl-2-(5-phenylethynyl-pyridin-2-yl)-5-trifluoromethyl-pyrazolidin-3-one.

One further embodiment of the invention provides compounds of formula IB

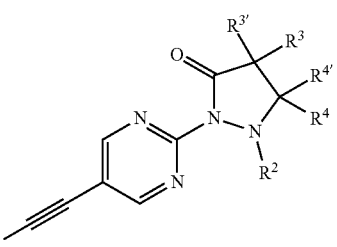

IB wherein
$R^1$ is phenyl or pyridyl, each of which is optionally substituted by halogen, lower alkyl or lower alkoxy;
$R^2$ is hydrogen or lower alkyl or together with $R^4$ form a $C_3$-$C_6$-cycloalkyl;
$R^3/R^{3'}/R^4/R^{4'}$ are each independently hydrogen, lower alkyl or $CF_3$;
or a pharmaceutically acceptable acid addition salt, a racemic mixture, or its corresponding enantiomer and/or optical isomer and/or stereoisomer thereof, for example the following compounds 5,5-dimethyl-2-(5-phenylethynyl-pyrimidin-2-yl)-pyrazolidin-3-one;
(RS)-1-(5-phenylethynyl-pyrimidin-2-yl)-tetrahydro-pyrrolo[1,2-b]pyrazol-2-one;
(RS)-1-[5-(3-fluoro-phenylethynyl)-pyrimidin-2-yl]-tetrahydro-pyrrolo[1,2-b]pyrazol-2-one;
(RS)-1-[5-(4-fluoro-phenylethynyl)-pyrimidin-2-yl]-tetrahydro-pyrrolo[1,2-b]pyrazol-2-one;
1,5,5-trimethyl-2-(5-phenylethynyl-pyrimidin-2-yl)-pyrazolidin-3-one;
2-[5-(3-fluoro-phenylethynyl)-pyrimidin-2-yl]-1,5,5-trimethyl-pyrazolidin-3-one;
2-[5-(4-fluoro-phenylethynyl)-pyrimidin-2-yl]-1,5,5-trimethyl-pyrazolidin-3-one and
2-[5-(2,5-difluoro-phenylethynyl)-pyrimidin-2-yl]-1,5,5-trimethyl-pyrazolidin-3-one.

One further embodiment of the invention provides compounds of formula IC

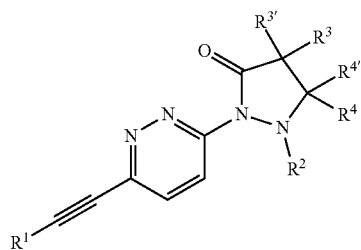

IC wherein
X is N or CH;
G is N or CH;
with the proviso that only one of X or G can be nitrogen;
$R^1$ is phenyl or pyridyl, each of which is optionally substituted by halogen, lower alkyl or lower alkoxy;
$R^2$ is hydrogen or lower alkyl or together with $R^4$ form a $C_3$-$C_6$-cycloalkyl;
$R^3/R^{3'}/R^4/R^{4'}$ are each independently hydrogen, lower alkyl or $CF_3$;
or a pharmaceutically acceptable acid addition salt, a racemic mixture, or its corresponding enantiomer and/or optical isomer and/or stereoisomer thereof, for example the following compound
2-[6-(2,5-difluoro-phenylethynyl)-pyridazin-3-yl]-5,5-dimethyl-pyrazolidin-3-one.

One further embodiment of the invention provides ethynyl derivatives of formula II

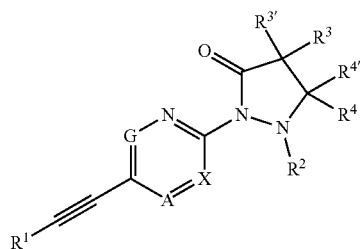

II wherein
X is N or C—$R^5$, wherein $R^5$ is hydrogen, methyl or halogen;
G and A are independently N or CH;
with the proviso that maximum one of X, G or A can be nitrogen;

$R^1$ is phenyl or heteroaryl, which are optionally substituted by halogen, lower alkyl or lower alkoxy;
$R^2$ is hydrogen, lower alkyl or together with $R^4$ form a $C_3$-$C_6$-cycloalkyl;
$R^3/R^{3'}/R^4/R^{4'}$ are independently from each other hydrogen, lower alkyl, $CH_2$-lower alkoxy;
or a pharmaceutically acceptable acid addition salt, a racemic mixture, or its corresponding enantiomer and/or optical isomer and/or stereoisomer thereof.

The preparation of compounds of formula I of the present invention can be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variants described below, which process comprises
a) reacting a compound of formula

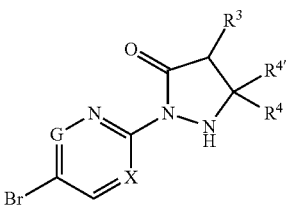

5 with a compound of formula

6 to form a compound of formula

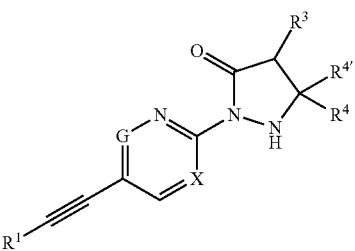

I-1 wherein the substituents are described above or b) reacting a compound of formula

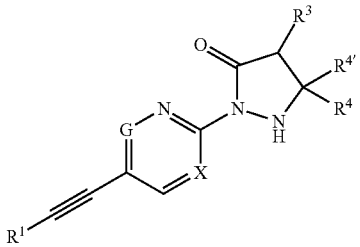

with a compound of formula $R^2$—X' wherein X' is Br or I,
to form a compound of formula

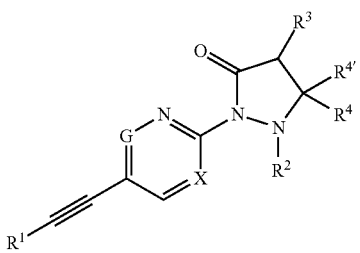

wherein the substituents are described above or
c) reacting a compound of formula

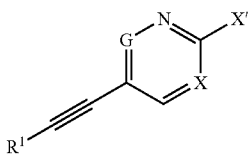

wherein X' is Br, I, F, I
with a compound of formula

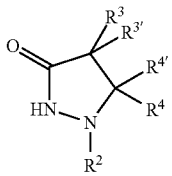

to form a compound of formula

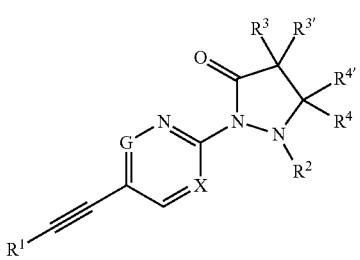

I wherein the substituents are described above, or if desired, converting the compounds obtained into pharmaceutically acceptable acid addition salts.

The preparation of compounds of formula I is further described in more detail in schemes 1 to 4 and in examples 1-24.

Scheme 1

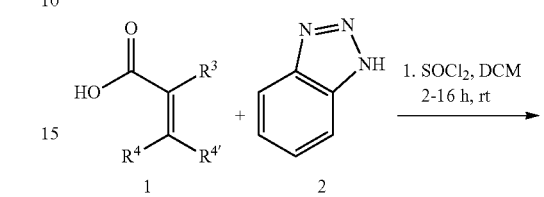

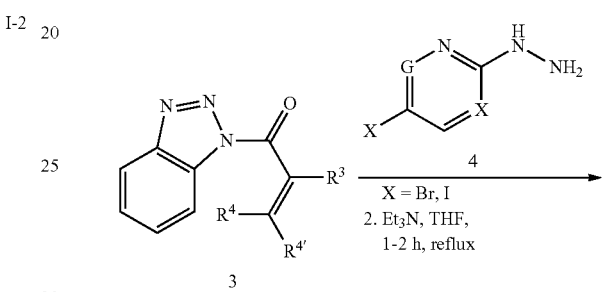

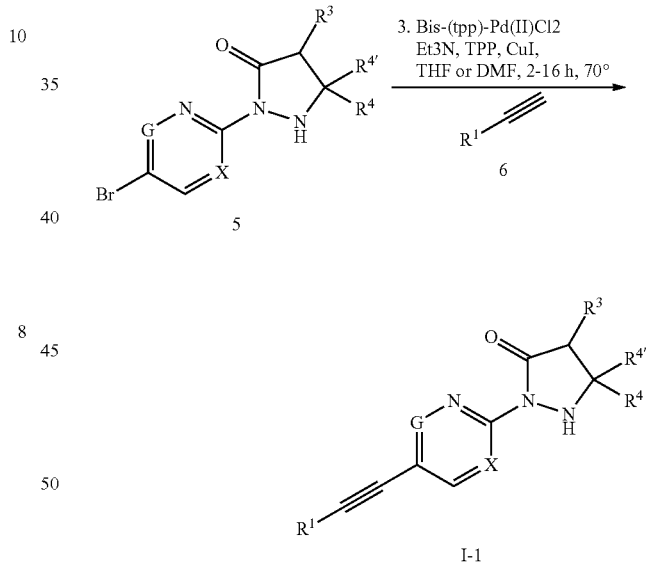

An ethynyl-pyridine or ethynyl-pyrimidine compound of formula I-1 can be obtained for example by reacting an appropriate α-β-unsaturated acid 1 with benzotriazole 2 in presence of a chlorinating agent such as $SOCl_2$ in a solvent like dichloromethane to yield the corresponding benzotriazole amide 3. Reaction of benzotriazole amide 3 with a 5-iodo- or 5-bromo-2-hydrazino heterocyclic derivative 4 in the presence of a base such as triethylamine in a solvent like THF yields the corresponding pyrazolidin-3-one derivatives 5. Sonogashira coupling of the pyrazolidin-3-one derivatives 5 with an appropriately substituted arylacetylene 6 yield the desired ethynyl compounds of formula I-1 (scheme 1).

Scheme 2

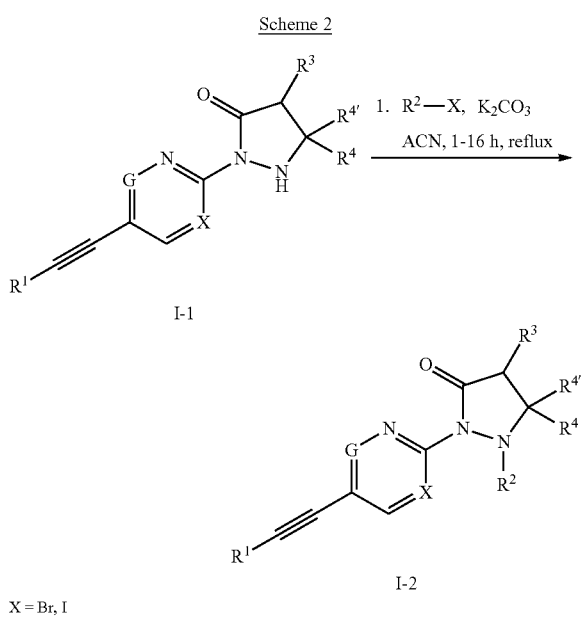

X = Br, I

An ethynyl-pyridine or ethynyl-pyrimidine compound of formula I-2 can be obtained for example by reacting a ethynyl compound of formula I-1 with an appropriate substituted alkylating agent in the presence of a base such as $K_2CO_3$ in a solvent like acetonitrile (ACN) to yield the desired ethynyl compounds of formula I-2 (scheme 2).

Scheme 3

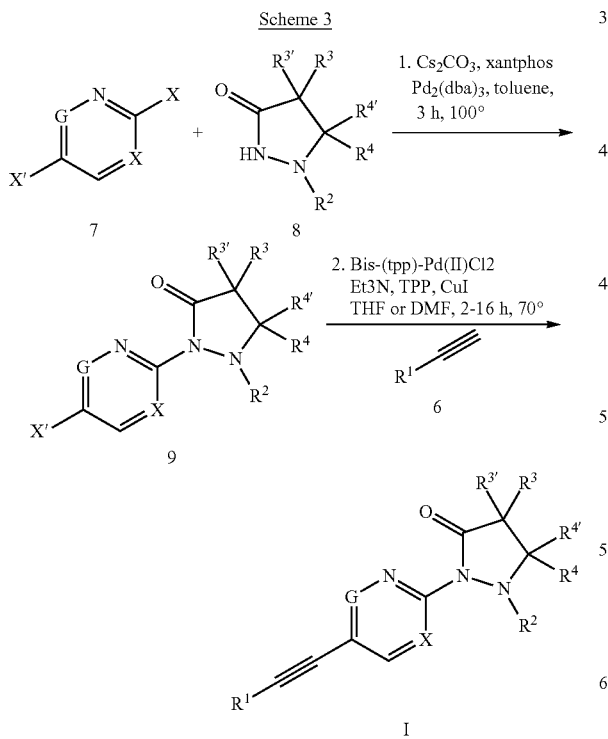

X = Br, I, F, Cl
X' = Br, I

An ethynyl compound of formula I can also be obtained by substitution of an appropriate para dihalosubstituted heterocyclic derivative 7 such as 2-bromo-5-iodopyridine, 5-iodo-2-fluoro-pyridine, 5-iodo-2-bromopyrimidine, 2-chloro-5-iodopyridazine or 2-bromo-5-iodopyrazine or the like and an appropriate pyrazolidin-3-one 8 in presence of a base such as cesium carbonate (X=Cl, F), or using palladium catalysed coupling conditions (X=Br,I) with appropriate ligands such as Xantphos and $Pd_2(dba)_3$ in a solvent like toluene to yield the corresponding 2-heteroaryl-pyrazolidin-3-one derivatives 9. Sonogashira coupling of 9 with an appropriately substituted arylacetylene 6 yields the desired ethynyl compounds of formula I (scheme 3).

Generally speaking, the sequence of steps used to synthesize the compounds of formula I-1, I-2 or I can also be modified in certain cases, for example by first running the Sonogashira coupling to form an appropriately substituted aryl- or heteroaryl-ethynyl derivative 10 followed by reaction with pyrazolidin-3-one 8 using procedures similar to those described in schemes 1 to 3 (scheme 4).

Scheme 4

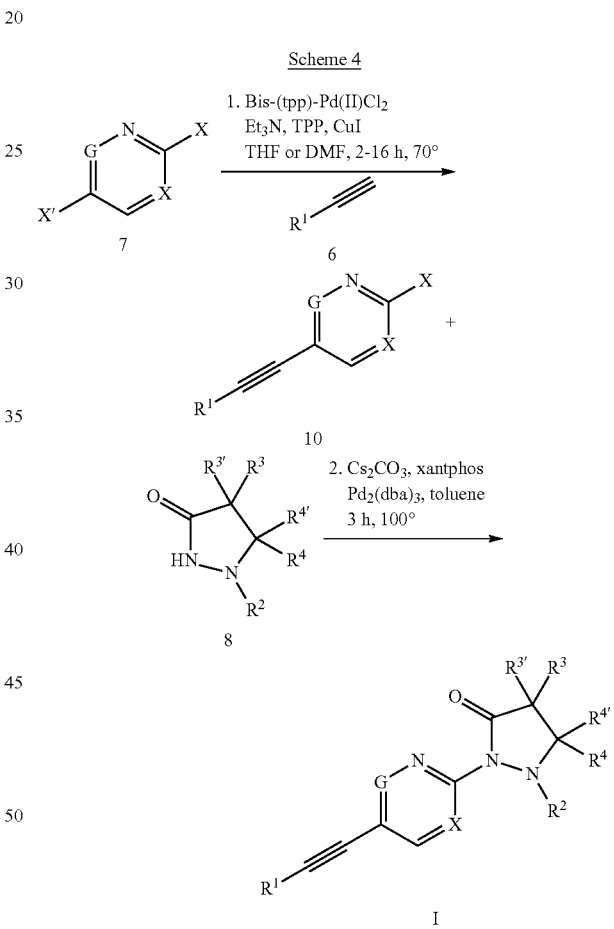

X = Br, I, F, Cl
X' = Br, I

Biological Assay and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min with on-line recording of fluorescence. Following this pre-incubation step, the agonist L-glutamate was added to the cells at a concentration corresponding to $EC_{20}$ (typically around 80 µM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was y=A+((B−A)/(1+((x/C)D))), where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the table below are shown the prepared compounds 1-24 with corresponding results ($EC_{50}$ in nM).

Examples 18, 20-22 have been tested on human mGluR5 receptor using the following method:

For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronized in 15 mM Tris-HCl, 120 mM NaCl, 100 mM KCl, 25 mM $CaCl_2$, 25 mM $MgCl_2$ binding buffer at pH 7.4 to a final assay concentration of 20 µg protein/well.

Saturation isotherms were determined by addition of twelve [$^3$H]MPEP concentrations (0.04-100 nM) to these membranes (in a total volume of 200 µl) for 1 h at 4° C. Competition experiments were performed with a fixed concentration of [$^3$H]MPEP (2 nM) and $IC_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 µM MPEP. The radioactivity on the filter was counted (3 min) on a Packard Top-count microplate scintillation counter with quenching correction after addition of 45 µl of microscint 40 (Canberra Packard S.A., Zürich, Switzerland) and shaking for 20 min.

For functional assays, [$Ca^{2+}$]i measurements were performed as described previously by Porter et al. [Br. J. Pharmacol. 128:13-20 (1999)] on recombinant human mGlu 5a receptors in HEK-293 cells. The cells were dye loaded using Fluo 4-AM (obtainable by FLUKA, 0.2 µM final concentration). [$Ca^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving $IC_{50}$, and Hill coefficient using an iterative non linear curve fitting software (Xcel fit).

For binding experiments the Ki values of the compounds tested are given. The Ki value is defined by the following formula:

$K_i = IC_{50}/[1+L/K_d]$ in which the $IC_{50}$ values are those concentrations of the compounds tested which cause 50% inhibition of the competing radioligand ([$^3$H]MPEP). L is the concentration of radioligand used in the binding experiment and the $K_d$ value of the radioligand is empirically determined for each batch of membranes prepared.

List of Examples:

| Ex. | Structure | Name | $EC_{50}$ (nM) mGlu5PAM | Eff. (%) |
|---|---|---|---|---|
| 1 | 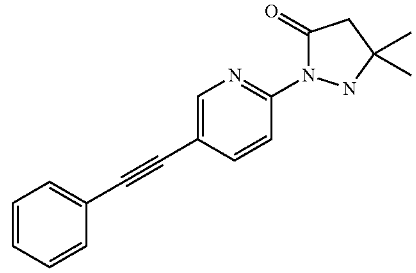 [SMILES: CC1(C)CC(=O)N(c2ccc(C#Cc3ccccc3)cn2)N1] | 5,5-Dimethyl-2-(5-phenylethynyl-pyridin-2-yl)-pyrazolidin-3-one | 7 | 60 |

-continued

| Ex. | Structure | Name | EC$_{50}$ (nM) mGlu5PAM | Eff. (%) |
|---|---|---|---|---|
| 2 | 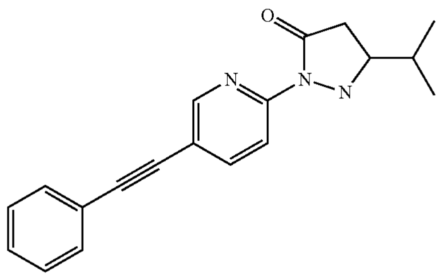 [SMILES: CC(C)C1CC(=O)N(c2ccc(C#Cc3ccccc3)cn2)N1] | (RS)-5-Isopropyl-2-(5-phenylethynyl-pyridin-2-yl)-pyrazolidin-3-one | 24 | 73 |
| 3 | 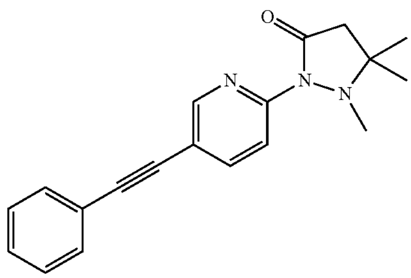 [SMILES: CN1N(c2ccc(C#Cc3ccccc3)cn2)C(=O)CC1(C)C] | 1,5,5-Trimethyl-2-(5-phenylethynyl-pyridin-2-yl)-pyrazolidin-3-one | 30 | 96 |
| 4 | 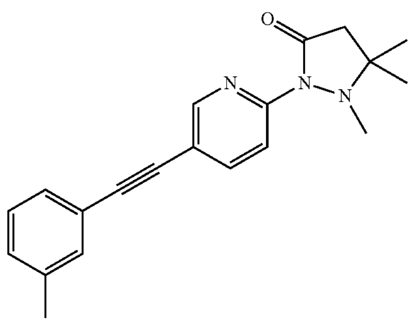 [SMILES: Cc1cccc(C#Cc2ccc(N3C(=O)CC(C)(C)N3C)nc2)c1] | 1,5,5-Trimethyl-2-(5-m-tolylethynyl-pyridin-2-yl)-pyrazolidin-3-one | 72 | 72 |
| 5 | 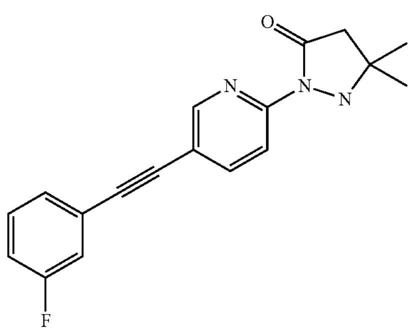 [SMILES: CC1(C)CC(=O)N(c2ccc(C#Cc3cccc(F)c3)cn2)N1] | 2-[5-(3-Fluoro-phenylethynyl)-pyridin-2-yl]-5,5-dimethyl-pyrazolidin-3-one | 13 | 31 |
| 6 | 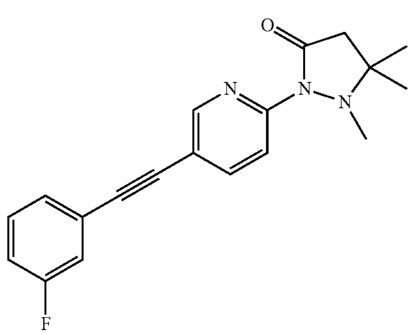 [SMILES: CN1N(c2ccc(C#Cc3cccc(F)c3)cn2)C(=O)CC1(C)C] | 2-[5-(3-Fluoro-phenylethynyl)-pyridin-2-yl]-1,5,5-trimethyl-pyrazolidin-3-one | 36 | 109 |

-continued

| Ex. | Structure | Name | EC₅₀ (nM) mGlu5PAM | Eff. (%) |
|---|---|---|---|---|
| 7 | 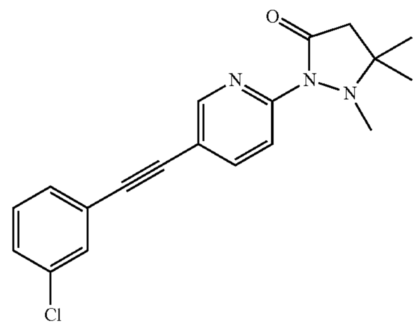 [SMILES: CN1N(c2ccc(C#Cc3cccc(Cl)c3)cn2)C(=O)CC1(C)C] | 2-[5-(3-Chloro-phenylethynyl)-pyridin-2-yl]-1,5,5-trimethyl-pyrazolidin-3-one | 90 | 55 |
| 8 | 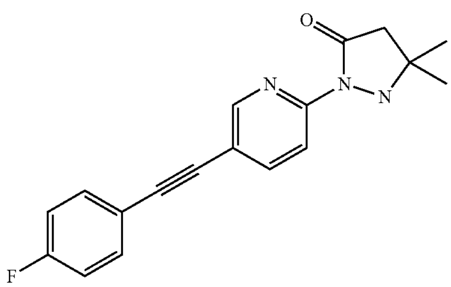 [SMILES: CC1(C)CC(=O)N(c2ccc(C#Cc3ccc(F)cc3)cn2)N1] | 2-[5-(4-Fluoro-phenylethynyl)-pyridin-2-yl]-5,5-dimethyl-pyrazolidin-3-one | 13 | 38 |
| 9 | 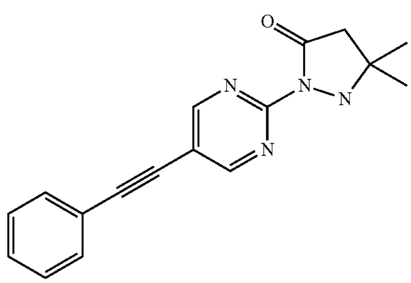 [SMILES: CC1(C)CC(=O)N(c2ncc(C#Cc3ccccc3)cn2)N1] | 5,5-Dimethyl-2-(5-phenylethynyl-pyrimidin-2-yl)-pyrazolidin-3-one | 46 | 39 |
| 10 | 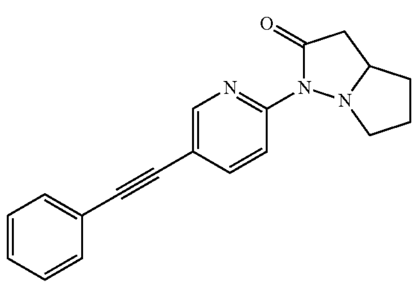 [SMILES: O=C1CC2CCCN2N1c1ccc(C#Cc2ccccc2)cn1] | (RS)-1-(5-Phenylethynyl-pyridin-2-yl)-tetrahydro-pyrrolo[1,2-b]pyrazol-2-one | 35 | 73 |
| 11 | 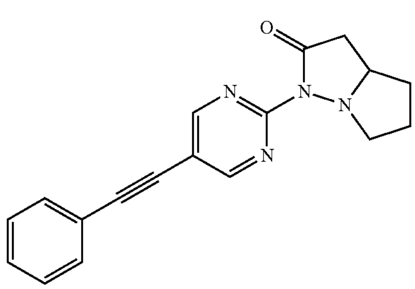 [SMILES: O=C1CC2CCCN2N1c1ncc(C#Cc2ccccc2)cn1] | (RS)-1-(5-Phenylethynyl-pyrimidin-2-yl)-tetrahydro-pyrrolo[1,2-b]pyrazol-2-one | 60 | 55 |

| Ex. | Structure | Name | EC$_{50}$ (nM) mGlu5PAM | Eff. (%) |
|---|---|---|---|---|
| 12 | 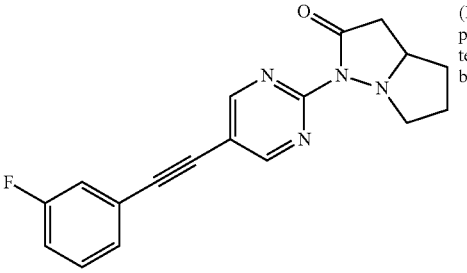 | (RS)-1-[5-(3-Fluoro-phenylethynyl)-pyrimidin-2-yl]-tetrahydro-pyrrolo[1,2-b]pyrazol-2-one | 22 | 59 |
| 13 | 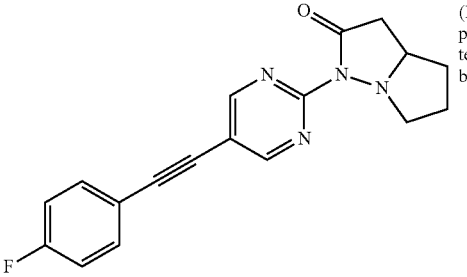 | (RS)-1-[5-(4-Fluoro-phenylethynyl)-pyrimidin-2-yl]-tetrahydro-pyrrolo[1,2-b]pyrazol-2-one | 41 | 58 |
| 14 | 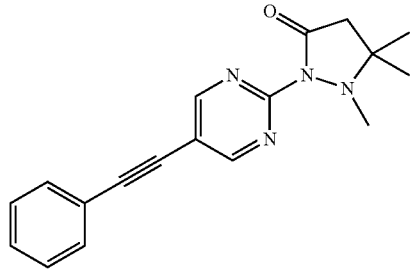 [SMILES: CN1N(c2ncc(C#Cc3ccccc3)cn2)C(=O)CC1(C)C] | 1,5,5-Trimethyl-2-(5-phenylethynyl-pyrimidin-2-yl)-pyrazolidin-3-one | 33 | 66 |
| 15 | 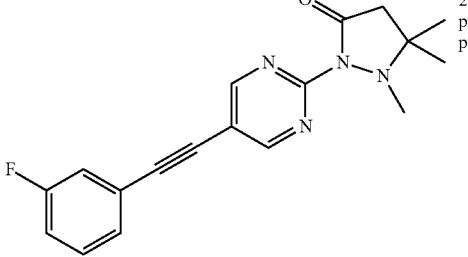 | 2-[5-(3-Fluoro-phenylethynyl)-pyrimidin-2-yl]-1,5,5-trimethyl-pyrazolidin-3-one | 34 | 61 |
| 16 | 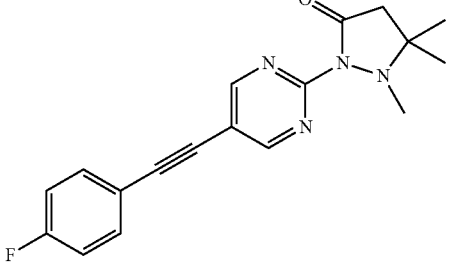 | 2-[5-(4-Fluoro-phenylethynyl)-pyrimidin-2-yl]-1,5,5-trimethyl-pyrazolidin-3-one | 56 | 69 |

-continued

| Ex. | Structure | Name | EC₅₀ (nM) mGlu5PAM | Eff. (%) |
|---|---|---|---|---|
| 17 | 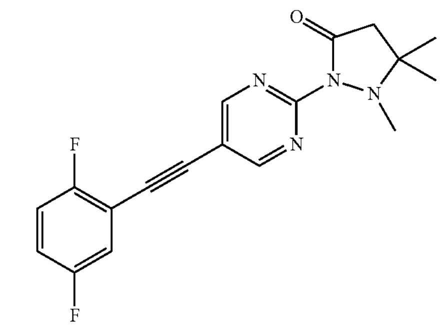 [SMILES: CN1N(c2ncc(C#Cc3cc(F)ccc3F)cn2)C(=O)CC1(C)C] | 2-[5-(2,5-Difluoro-phenylethynyl)-pyrimidin-2-yl]-1,5,5-trimethyl-pyrazolidin-3-one | 35 | 47 |
| 18 | 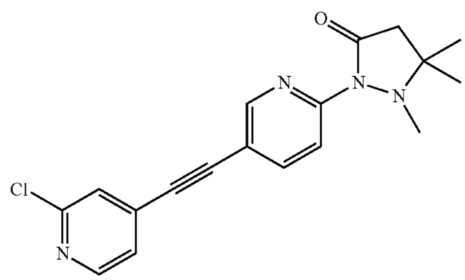 [SMILES: CN1N(c2ccc(C#Cc3ccnc(Cl)c3)cn2)C(=O)CC1(C)C] | 2-[5-(2-Chloro-pyridin-4-ylethynyl)-pyridin-2-yl]-1,5,5-trimethyl-pyrazolidin-3-one | Human mGluR5 Ki [nM] = 103 nM | |
| 19 | 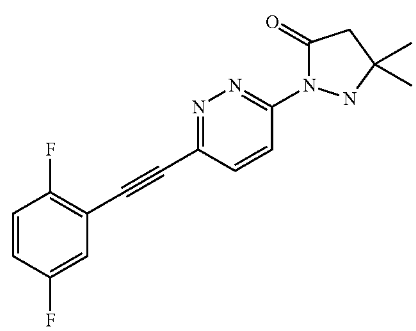 [SMILES: CC1(C)CC(=O)N(c2ccc(C#Cc3cc(F)ccc3F)nn2)N1] | 2-[6-(2,5-Difluoro-phenylethynyl)-pyridazin-3-yl]-5,5-dimethyl-pyrazolidin-3-one | 86 | 86 |
| 20 | 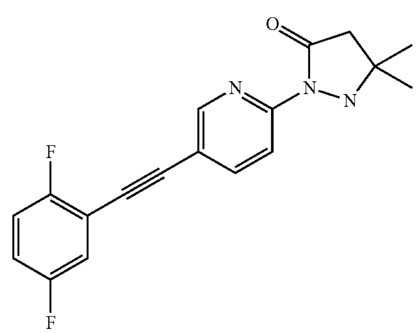 [SMILES: CC1(C)CC(=O)N(c2ccc(C#Cc3cc(F)ccc3F)cn2)N1] | 2-[5-(2,5-Difluoro-phenylethynyl)-pyridin-2-yl]-5,5-dimethyl-pyrazolidin-3-one | Human mGluR5 Ki [nM] = 69.7 nM pKi = 7.157 | |
| 21 | 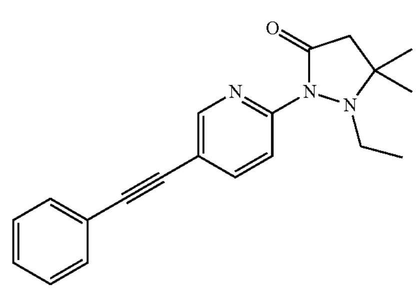 [SMILES: CCN1N(c2ccc(C#Cc3ccccc3)cn2)C(=O)CC1(C)C] | 1-Ethyl-5,5-dimethyl-2-(5-phenylethynyl-pyridin-2-yl)-pyrazolidin-3-one | Human mGluR5 Ki [nM] = 53.5 nM pKi = 7.272 | |

-continued

| Ex. | Structure | Name | EC$_{50}$ (nM) mGlu5PAM | Eff. (%) |
|---|---|---|---|---|
| 22 | 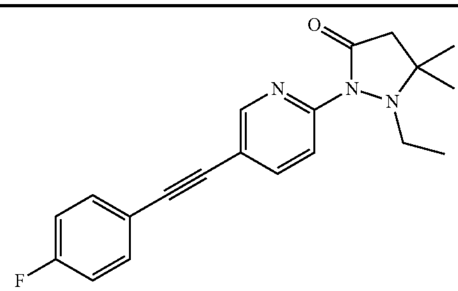 | 1-Ethyl-2-[5-(4-fluoro-phenylethynyl)-pyridin-2-yl]-5,5-dimethyl-pyrazolidin-3-one | Human mGluR5 Ki [nM] = 54.3 nM pKi = 7.266 | |
| 23 | 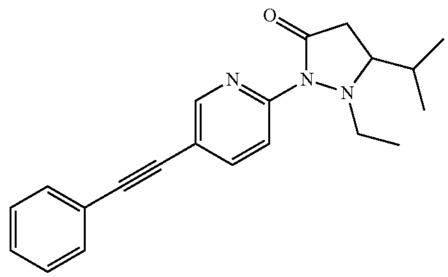 [SMILES: CCN1C(C(C)C)CC(=O)N1c1ccc(C#Cc2ccccc2)cn1] | (RS)-1-Ethyl-5-isopropyl-2-(5-phenylethynyl-pyridin-2-yl)-pyrazolidin-3-one | 106 | 46 |
| 24 | 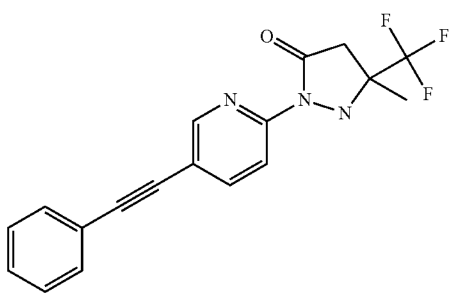 [SMILES: CC1(C(F)(F)F)CC(=O)N(c2ccc(C#Cc3ccccc3)cn2)N1] | (RS)-5-Methyl-2-(5-phenylethynyl-pyridin-2-yl)-5-trifluoromethyl-pyrazolidin-3-one | 71 | 92 |

The compounds of formula (I) and pharmaceutically acceptable salts thereof can be used as therapeutics, e.g. in the form of pharmaceutical compositions. The pharmaceutical compositions can be administered orally, e.g. in the form of tablets, coated tablets, dragées, hard and soft gelatin capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, the present invention provides pharmaceutical compositions containing a compound of formula (I) or pharmaceutically acceptable salts thereof and a therapeutically inert excipient, as is a process for the production of such pharmaceutical compositions which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the present invention provides for the use of the compounds of formula (I) for the preparation of pharmaceutical compositions useful in the prevention and/or the treatment of the above recited diseases.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions
Comprising Compounds of the Invention Example A Tablets of the following composition are produced in a conventional manner:

|  | mg/Tablet |
|---|---|
| Active ingredient | 100 |
| Powdered. Lactose | 95 |
| White corn starch | 35 |
| Polyvinylpyrrolidone | 8 |
| Na carboxymethylstarch | 10 |
| Magnesium stearate | 2 |
| Tablet weight | 250 |

EXPERIMENTAL SECTION

Example 1

5,5-Dimethyl-2-(5-phenylethynyl-pyridin-2-yl)-pyrazolidin-3-one

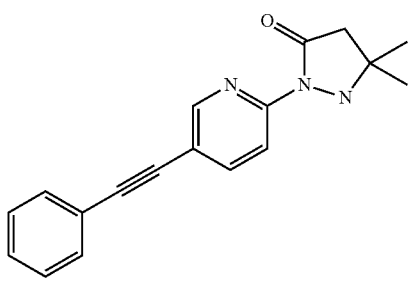 [SMILES: CC1(C)CC(=O)N(c2ccc(C#Cc3ccccc3)cn2)N1]

Step 1: 1-Benzotriazol-1-yl-3-methyl-but-2-en-1-one

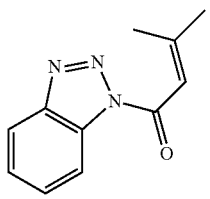

1H-Benzotriazole (2.14 g, 18.0 mmol, 4 equiv.) was dissolved in dichloromethane (25 ml) and thionyl chloride (330 μl, 4.5 mmol, 1 equiv.) was added at room temperature. (450 mg, 4.5 mmol) 3-Methyl-but-2-enoic acid [CAS 541-47-9] was added and the mixture was stirred for 2 hours at room temperature. The suspension was filtered and the filtrate was extracted once with 2N NaOH solution and twice with dichloromethane. The organic extracts were combined, dried over sodium sulfate and evaporated to dryness. The crude product was purified by flash chromatography on a silica gel column eluting with an ethyl acetate:cyclohexane gradient 0:100 to 50:50. The desired 1-benzotriazol-1-yl-3-methyl-but-2-en-1-one (810 mg, 90% yield) was obtained as a light yellow solid, MS: m/e=202.1 (M+H$^+$).

Step 2: 2-(5-Bromo-pyridin-2-yl)-5,5-dimethyl-pyrazolidin-3-one

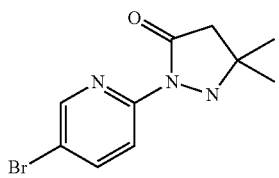

(400 mg, 2.0 mmol) 1-Benzotriazol-1-yl-3-methyl-but-2-en-1-one (Example 1, step 1), (5-bromo-pyridin-2-yl)-hydrazine (410 mg, 2.2 mmol, 1.1 equiv.) and Et$_3$N (1.95 ml, 14.0 mmol, 7 equiv.) were dissolved together in THF (2 ml) and stirred for 90 minutes at reflux temperature. The reaction mixture was cooled and extracted with saturated Na$_2$CO$_3$ solution and two times with ethyl acetate. The organic extracts were extracted with brine, dried over sodium sulfate and evaporated to dryness. The crude product was purified by flash chromatography on a silica gel column eluting with an ethyl acetate:cyclohexane gradient 0:100 to 50:50. The desired 2-(5-bromo-pyridin-2-yl)-5,5-dimethyl-pyrazolidin-3-one (230 mg, 43% yield) was obtained as a yellow oil, MS: m/e=270.2/272.2 (M+H$^+$).

Step 3: 5,5-Dimethyl-2-(5-phenylethynyl-pyridin-2-yl)-pyrazolidin-3-one

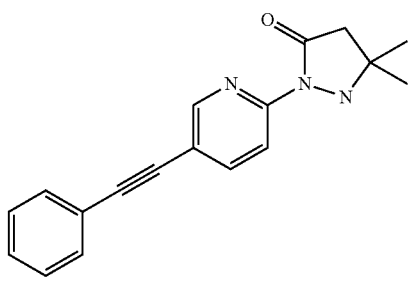 [SMILES: CC1(C)CC(=O)N(c2ccc(C#Cc3ccccc3)cn2)N1]

Bis-(triphenylphosphine)-palladium(II)dichloride (27 mg, 39 μmol, 0.05 equiv.) was dissolved in 2 ml THF. (210 mg, 770 μmol) 2-(5-Bromo-pyridin-2-yl)-5,5-dimethyl-pyrazolidin-3-one (Example 1, step 2) and phenylacetylene (130 mg, 1.24 mmol, 1.6 equiv.) were added at room temperature. Triethylamine (325 μl, 2.33 mmol, 3 equiv.), triphenylphosphine (6 mg, 23.3 μmol, 0.03 equiv.) and copper(I)iodide (4 mg, 23.3 μmol, 0.03 equiv.) were added and the mixture was stirred for 16 hours at 65° C. The reaction mixture was cooled and extracted with saturated NaHCO$_3$ solution and two times with a small volume of dichloromethane. The crude product was purified by flash chromatography by directly loading the dichloromethane layers onto a silica gel column eluting with an ethyl acetate:heptane gradient 0:100 to 100:0. The desired 5,5-dimethyl-2-(5-phenylethynyl-pyridin-2-yl)-pyrazolidin-3-one (102 mg, 45% yield) was obtained as a white solid, MS: m/e=292.1 (M+H$^+$).

Example 2

(RS)-5-Isopropyl-2-(5-phenylethynyl-pyridin-2-yl)-pyrazolidin-3-one

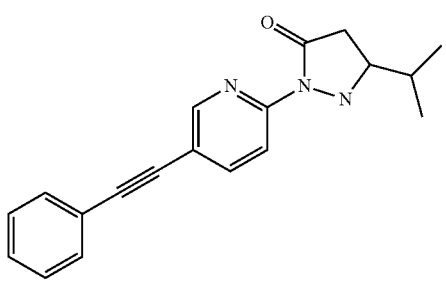 [SMILES: CC(C)C1CC(=O)N(c2ccc(C#Cc3ccccc3)cn2)N1]

Step 1: (E/Z)-1-Benzotriazol-1-yl-4-methyl-pent-2-en-1-one

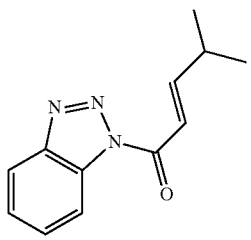 [SMILES: CC(C)/C=C/C(=O)n1nnc2ccccc21]

The title compound was obtained as a colorless liquid, MS: m/e=215 (M+H$^+$), using chemistry similar to that described in Example 1, step 1 from 4-methyl-pent-2-enoic acid [CAS 10321-71-8] and 1H-benzotriazole.

Step 2: (RS)-2-(5-Bromo-pyridin-2-yl)-5-isopropyl-pyrazolidin-3-one

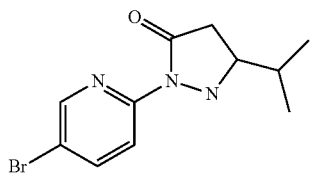 [SMILES: CC(C)C1CC(=O)N(c2ccc(Br)cn2)N1]

The title compound was obtained as a light yellow oil, MS: m/e=284.0/286.0 (M+H$^+$), using chemistry similar to that described in Example 1, step 2 from (E/Z)-1-benzotriazol-1-yl-4-methyl-pent-2-en-1-one (Example 2, step 1) and (5-bromo-pyridin-2-yl)-hydrazine.

Step 3: (RS)-5-Isopropyl-2-(5-phenylethynyl-pyridin-2-yl)-pyrazolidin-3-one

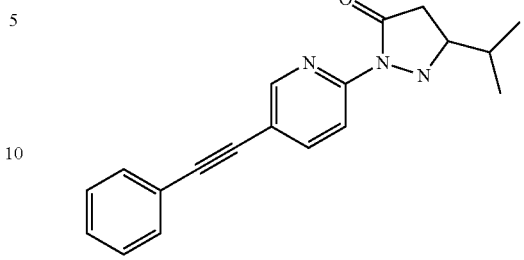

The title compound was obtained as a light yellow oil, MS: m/e=306.1 (M+H$^+$), using chemistry similar to that described in Example 1, step 3 from (RS)-2-(5-bromo-pyridin-2-yl)-5-isopropyl-pyrazolidin-3-one (Example 2, step 2) and phenylacetylene.

Example 3

1,5,5-Trimethyl-2-(5-phenylethynyl-pyridin-2-yl)-pyrazolidin-3-one

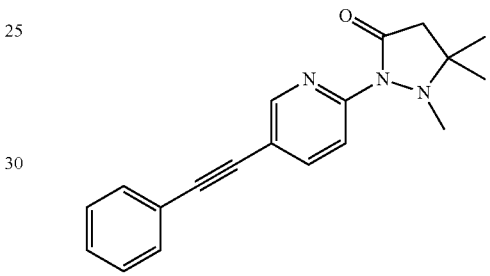

(35 mg, 120 μmol) 5,5-Dimethyl-2-(5-phenylethynyl-pyridin-2-yl)-pyrazolidin-3-one (Example 1, step 4) was dissolved in ACN (2 ml). K$_2$CO$_3$ (33 mg, 240 μmol, 2 equiv.) and iodomethane (22 mg, 156 μmol, 1.3 equiv.) were added and the mixture was stirred for 16 hours at 80° C. The reaction mixture was evaporated and extracted with water and two times with ethyl acetate. The organic layers were extracted with brine, dried with sodium sulfate and evaporated to dryness. The crude product was purified by reverse phase column chromatography. The desired 1,5,5-trimethyl-2-(5-phenylethynyl-pyridin-2-yl)-pyrazolidin-3-one (18 mg, 49% yield) was obtained as a colorless oil, MS: m/e=306.2 (M+H$^+$).

Example 4

1,5,5-Trimethyl-2-(5-m-tolylethynyl-pyridin-2-yl)-pyrazolidin-3-one

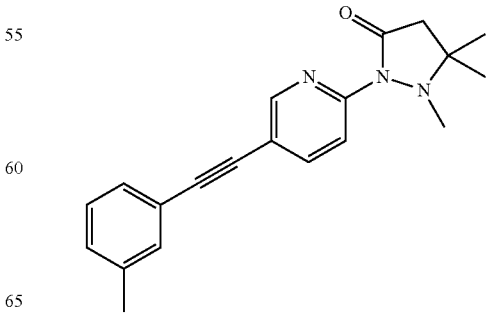

Step 1: 5,5-Dimethyl-2-(5-m-tolylethynyl-pyridin-2-yl)-pyrazolidin-3-one

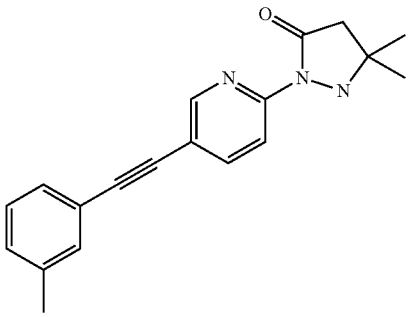 [SMILES: Cc1cccc(C#Cc2ccc(N3NC(C)(C)CC3=O)nc2)c1]

The title compound was obtained as a brown oil, MS: m/e=306.2 (M+H$^+$), using chemistry similar to that described in Example 1, step 3 from 2-(5-bromo-pyridin-2-yl)-5,5-dimethyl-pyrazolidin-3-one (Example 1, step 2) and m-tolylacetylene.

Step 2: 1,5,5-Trimethyl-2-(5-m-tolylethynyl-pyridin-2-yl)-pyrazolidin-3-one

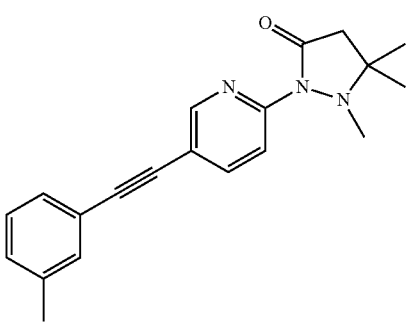 [SMILES: Cc1cccc(C#Cc2ccc(N3C(=O)CC(C)(C)N3C)nc2)c1]

The title compound was obtained as a white solid, MS: m/e=320.2 (M+H$^+$), using chemistry similar to that described in Example 3 from 5,5-dimethyl-2-(5-m-tolylethynyl-pyridin-2-yl)-pyrazolidin-3-one (Example 4, step 1).

Example 5

2-[5-(3-Fluoro-phenylethynyl)-pyridin-2-yl]-5,5-dimethyl-pyrazolidin-3-one

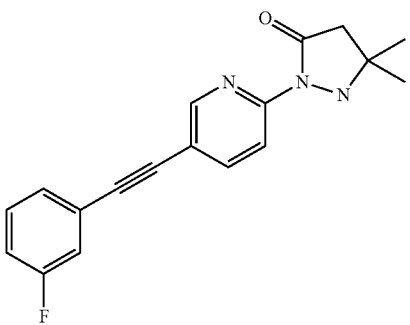 [SMILES: CC1(C)CC(=O)N(c2ccc(C#Cc3cccc(F)c3)cn2)N1]

The title compound was obtained as a light yellow solid, MS: m/e=310.2 (M+H$^+$), using chemistry similar to that described in Example 1, step 3 from 2-(5-bromo-pyridin-2-yl)-5,5-dimethyl-pyrazolidin-3-one (Example 1, step 2) and 1-ethynyl-3-fluoro-benzene.

Example 6

2-[5-(3-Fluoro-phenylethynyl)-pyridin-2-yl]-1,5,5-trimethyl-pyrazolidin-3-one

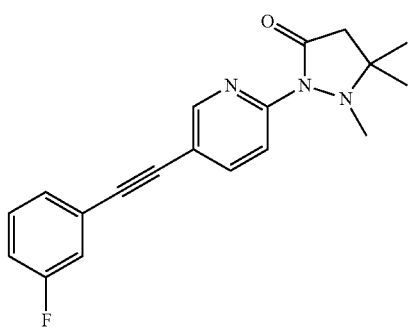 [SMILES: CN1N(c2ccc(C#Cc3cccc(Cl)c3)cn2)C(=O)CC1(C)C]

The title compound was obtained as a colorless oil, MS: m/e=324.2 (M+H$^+$), using chemistry similar to that described in Example 3 from 2-[5-(3-fluoro-phenylethynyl)-pyridin-2-yl]-5,5-dimethyl-pyrazolidin-3-one (Example 5).

Example 7

2-[5-(3-Chloro-phenylethynyl)-pyridin-2-yl]-1,5,5-trimethyl-pyrazolidin-3-one

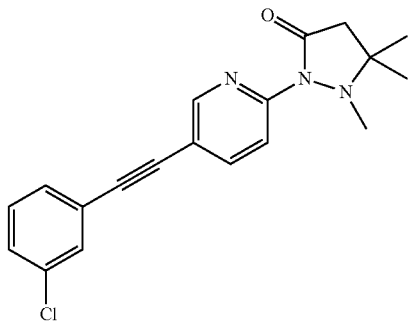 [SMILES: CN1N(c2ccc(C#Cc3cccc(Cl)c3)cn2)C(=O)CC1(C)C]

Step 1: 2-[5-(3-Chloro-phenylethynyl)-pyridin-2-yl]-5,5-dimethyl-pyrazolidin-3-one

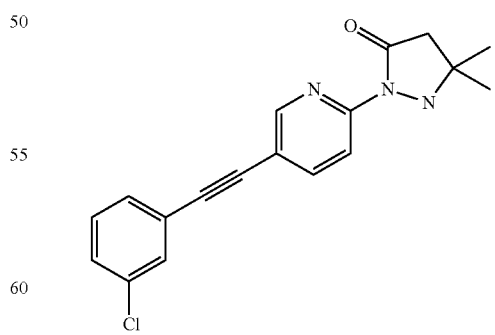

The title compound was obtained as a yellow solid, MS: m/e=326.1/328.1 (M+H$^+$), using chemistry similar to that described in Example 1, step 3 from 2-(5-bromo-pyridin-2-yl)-5,5-dimethyl-pyrazolidin-3-one (Example 1, step 2) and 1-ethynyl-3-chloro-benzene.

Step 2: 2-[5-(3-Chloro-phenylethynyl)-pyridin-2-yl]-1,5,5-trimethyl-pyrazolidin-3-one

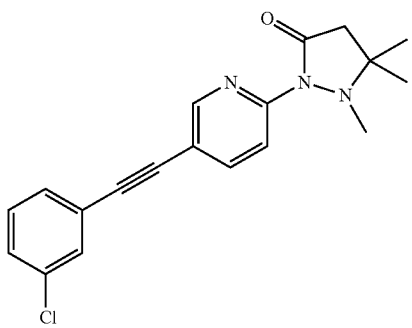

The title compound was obtained as a white solid, MS: m/e=340.1/342.1 (M+H⁺), using chemistry similar to that described in Example 3 from 2-[5-(3-chloro-phenylethynyl)-pyridin-2-yl]-5,5-dimethyl-pyrazolidin-3-one (Example 7, step 1).

Example 8

2-[5-(4-Fluoro-phenylethynyl)-pyridin-2-yl]-5,5-dimethyl-pyrazolidin-3-one

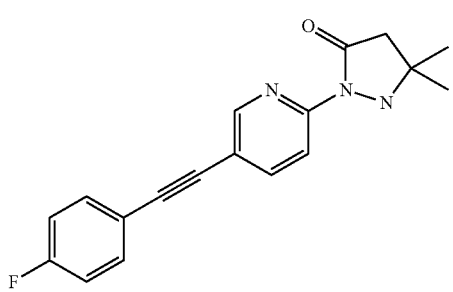 [SMILES: CC1(C)CC(=O)N(c2ccc(C#Cc3ccc(F)cc3)cn2)N1]

The title compound was obtained as a white solid, MS: m/e=310.1 (M+H⁺), using chemistry similar to that described in Example 1, step 3 from 2-(5-bromo-pyridin-2-yl)-5,5-dimethyl-pyrazolidin-3-one (Example 1, step 2) and 1-ethynyl-4-fluoro-benzene.

Example 9

5,5-Dimethyl-2-(5-phenylethynyl-pyrimidin-2-yl)-pyrazolidin-3-one

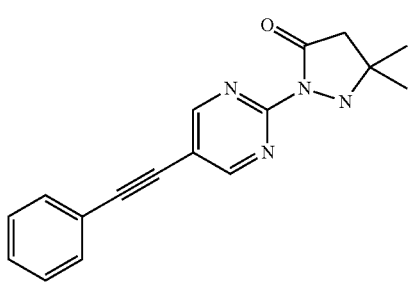 [SMILES: CC1(C)CC(=O)N(c2ncc(C#Cc3ccccc3)cn2)N1]

Step 1: 2-(5-Bromo-pyrimidin-2-yl)-5,5-dimethyl-pyrazolidin-3-one

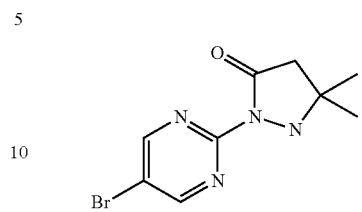

The title compound was obtained as a light yellow solid, MS: m/e=271.2/273.1 (M+H⁺), using chemistry similar to that described in Example 1, step 2 from 1-benzotriazol-1-yl-3-methyl-but-2-en-1-one (Example 1, step 1) and (5-bromo-pyrimidin-2-yl)-hydrazine.

Step 2: 5,5-Dimethyl-2-(5-phenylethynyl-pyrimidin-2-yl)-pyrazolidin-3-one

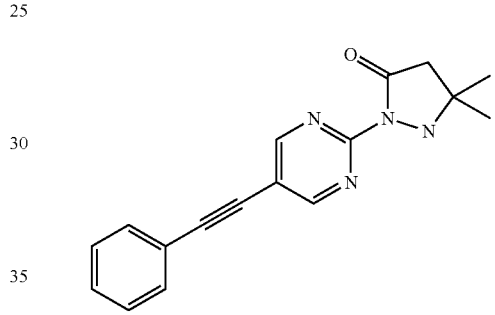

The title compound was obtained as a light grey solid, MS: m/e=293.2 (M+H⁺), using chemistry similar to that described in Example 1, step 3 from 2-(5-bromo-pyrimidin-2-yl)-5,5-dimethyl-pyrazolidin-3-one (Example 9, step 1) and phenylacetylene.

Example 10

(RS)-1-(5-Phenylethynyl-pyridin-2-yl)-tetrahydro-pyrrolo[1,2-b]pyrazol-2-one

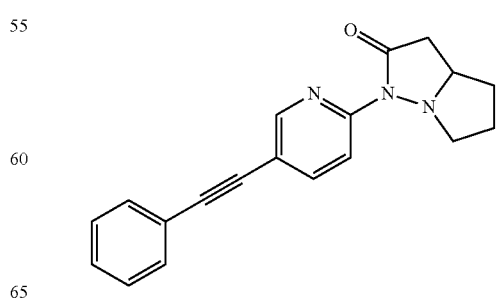

Step 1: 2-Bromo-5-phenylethynyl-pyridine

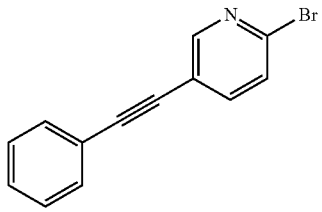 [SMILES: Brc1ccc(C#Cc2ccccc2)cn1]

The title compound was obtained as a white solid, MS: m/e=258/260 (M+H$^+$), using chemistry similar to that described in Example 1, step 3 from 2-bromo-5-iodopyridine and phenylacetylene.

Step 2: (RS)-1-(5-Phenylethynyl-pyridin-2-yl)-tetrahydro-pyrrolo[1,2-b]pyrazol-2-one

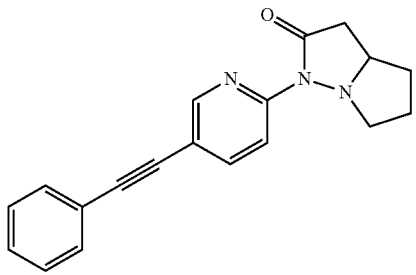 [SMILES: O=C1CC2CCCN2N1c1ccc(C#Cc2ccccc2)cn1]

(150 mg, 0.58 mmol) 2-Bromo-5-phenylethynyl-pyridine (Example 10, step 1) was dissolved in toluene (2 ml) and (RS)-tetrahydro-pyrrolo[1,2-b]pyrazol-2-one [CAS 1159091-93-6] (73 mg, 0.58 mmol, 1.0 equiv.), cesium carbonate (280 mg, 0.87 mmol, 1.5 equiv.), xantphos [CAS 161265-03-8] (14 mg, 0.02 mmol, 0.04 equiv.) and Pd$_2$(dba)$_3$ (11 mg, 0.01 mmol, 0.02 equiv.) were added under nitrogen. The mixture was stirred for 3 hours at 100° C. The crude product was purified by flash chromatography by directly loading the toluene mixture onto a silica gel column and eluting with an ethyl acetate:heptane gradient 0:100 to 100:0. The desired (RS)-1-(5-phenylethynyl-pyridin-2-yl)-tetrahydro-pyrrolo[1,2-b]pyrazol-2-one (17 mg, 9% yield) was obtained as a light brown solid, MS: m/e=304.1 (M+H$^+$).

Example 11

(RS)-1-(5-Phenylethynyl-pyrimidin-2-yl)-tetrahydro-pyrrolo[1,2-b]pyrazol-2-one

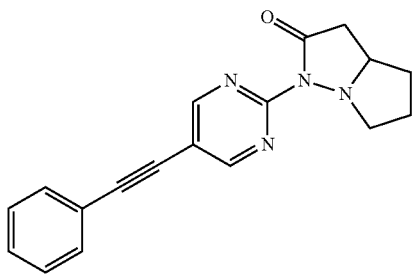 [SMILES: O=C1CC2CCCN2N1c1ncc(C#Cc2ccccc2)cn1]

Step 1: 2-Bromo-5-phenylethynyl-pyrimidine

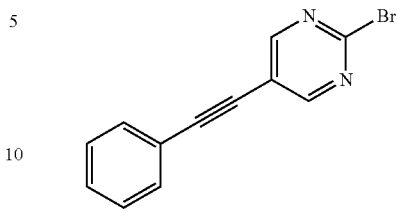

The title compound was obtained as a white solid, MS: m/e=259.0/261.0 (M+H$^+$), using chemistry similar to that described in Example 1, step 3 from 2-bromo-5-iodopyrimidine (CAS 905856-70-4) and phenylacetylene.

Step 2: (RS)-1-(5-Phenylethynyl-pyrimidin-2-yl)-tetrahydro-pyrrolo[1,2-b]pyrazol-2-one

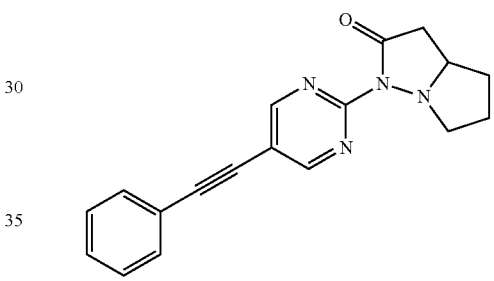

The title compound was obtained as a brown solid, MS: m/e=305.1 (M+H$^+$), using chemistry similar to that described in Example 10, step 2 from 2-bromo-5-phenylethynyl-pyrimidine (Example 11, step 1) and (RS)-tetrahydro-pyrrolo[1,2-b]pyrazol-2-one (CAS 1159091-93-6).

Example 12

(RS)-1-[5-(3-Fluoro-phenylethynyl)-pyrimidin-2-yl]-tetrahydro-pyrrolo[1,2-b]pyrazol-2-one

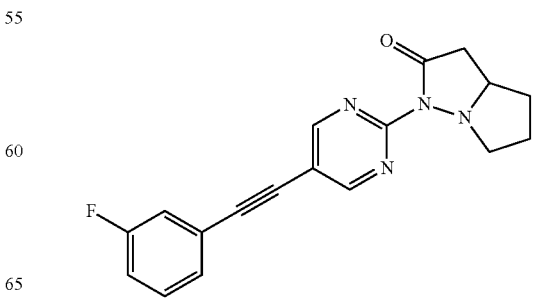

Step 1: (RS)-1-(5-Bromo-pyrimidin-2-yl)-tetrahydro-pyrrolo[1,2-b]pyrazol-2-one

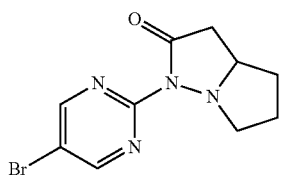 [SMILES: O=C1CC2CCCN2N1c1ncc(Br)cn1]

The title compound was obtained as a yellow solid, MS: m/e=283.0/285.0 (M+H⁺), using chemistry similar to that described in Example 10, step 2 from 2-iodo-5-bromopyrimidine and (RS)-tetrahydro-pyrrolo[1,2-b]pyrazol-2-one (CAS 1159091-93-6).

Step 2: (RS)-1-[5-(3-Fluoro-phenylethynyl)-pyrimidin-2-yl]-tetrahydro-pyrrolo[1,2-b]pyrazol-2-one

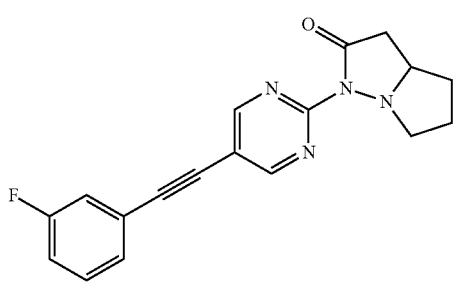 [SMILES: O=C1CC2CCCN2N1c1ncc(C#Cc2cccc(F)c2)cn1]

The title compound was obtained as a light yellow solid, MS: m/e=323.1 (M+H⁺), using chemistry similar to that described in Example 1, step 3 from (RS)-1-(5-bromo-pyrimidin-2-yl)-tetrahydro-pyrrolo[1,2-b]pyrazol-2-one (Example 12, step 1) and 3-fluorophenylacetylene.

Example 13

(RS)-1-[5-(4-Fluoro-phenylethynyl)-pyrimidin-2-yl]-tetrahydro-pyrrolo[1,2-b]pyrazol-2-one

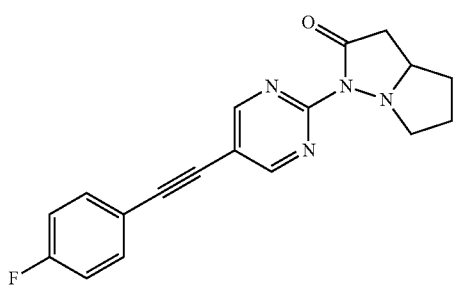 [SMILES: O=C1CC2CCCN2N1c1ncc(C#Cc2ccc(F)cc2)cn1]

The title compound was obtained as a yellow solid, MS: m/e=323.1 (M+H⁺), using chemistry similar to that described in Example 1, step 3 from (RS)-1-(5-bromo-pyrimidin-2-yl)-tetrahydro-pyrrolo[1,2-b]pyrazol-2-one (Example 12, step 1) and 4-fluorophenylacetylene.

Example 14

1,5,5-Trimethyl-2-(5-phenylethynyl-pyrimidin-2-yl)-pyrazolidin-3-one

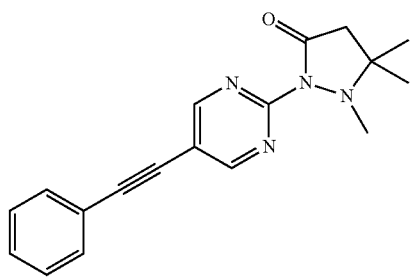 [SMILES: CN1N(c2ncc(C#Cc3ccccc3)cn2)C(=O)CC1(C)C]

The title compound was obtained as a brown solid, MS: m/e=307.2 (M+H⁺), using chemistry similar to that described in Example 3 from 5,5-dimethyl-2-(5-phenylethynyl-pyrimidin-2-yl)-pyrazolidin-3-one (Example 9, step 2) and iodomethane.

Example 15

2-[5-(3-Fluoro-phenylethynyl)-pyrimidin-2-yl]-1,5,5-trimethyl-pyrazolidin-3-one

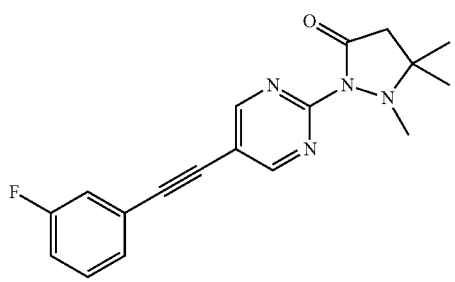 [SMILES: CN1N(c2ncc(C#Cc3cccc(F)c3)cn2)C(=O)CC1(C)C]

Step 1:
5,5-Dimethyl-3-oxo-pyrazolidine-1-carboxylic acid tert-butyl ester

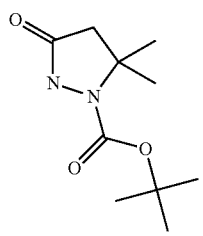

The title compound was obtained as a white solid, MS: m/e=215.2 (M+H⁺), using chemistry similar to that described in the Literature Tetrahedron 66 (2010) Page 8992-9008 from 5,5-dimethyl-pyrazolidin-3-one (CAS 24572-33-6).

Step 2: 2-(5-Bromo-pyrimidin-2-yl)-5,5-dimethyl-3-oxo-pyrazolidine-1-carboxylic acid tert-butyl ester

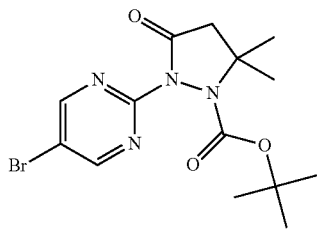 [SMILES: CC(C)(C)OC(=O)N1N(c2ncc(Br)cn2)C(=O)CC1(C)C]

The title compound was obtained as a yellow solid, MS: m/e=371.1/373.0 (M+H⁺), using chemistry similar to that described in Example 10, step 2 from 2-iodo-5-bromopyrimidine and 5,5-dimethyl-3-oxo-pyrazolidine-1-carboxylic acid tert-butyl ester (Example 15, step 1).

Step 3: 2-[5-(3-Fluoro-phenylethynyl)-pyrimidin-2-yl]-5,5-dimethyl-3-oxo-pyrazolidine-1-carboxylic acid tert-butyl ester

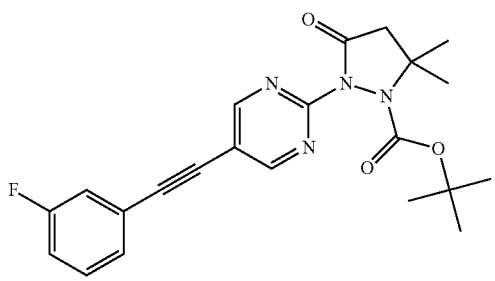 [SMILES: CC(C)(C)OC(=O)N1N(c2ncc(C#Cc3cccc(F)c3)cn2)C(=O)CC1(C)C]

The title compound was obtained as a brown solid, MS: m/e=411.2 (M+H⁺), using chemistry similar to that described in Example 1, step 3 from 2-(5-bromo-pyrimidin-2-yl)-5,5-dimethyl-3-oxo-pyrazolidine-1-carboxylic acid tert-butyl ester (Example 15, step 2) and 3-fluorophenylacetylene.

Step 4: 2-[5-(3-Fluoro-phenylethynyl)-pyrimidin-2-yl]-5,5-dimethyl-pyrazolidin-3-one

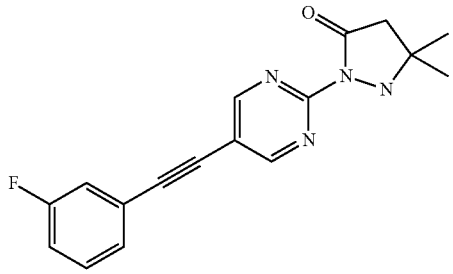

(118 mg, 0.29 mmol) 2-[5-(3-Fluoro-phenylethynyl)-pyrimidin-2-yl]-5,5-dimethyl-3-oxo-pyrazolidine-1-carboxylic acid tert-butyl ester (Example 15, step 3) was dissolved in dichloromethane (2 ml) and TFA (0.55 ml, 7.2 mmol, 25 equiv.) was added at room temperature and stirred for 16 hours. The reaction mixture was extracted with saturated Na₂CO₃ solution and a small amount of dichloromethane. The organic extract was loaded directly to a silica gel column. The crude product was purified by flash chromatography on a silica gel column eluting with an ethyl acetate:heptane gradient 0:100 to 100:0. The desired 2-[5-(3-fluoro-phenylethynyl)-pyrimidin-2-yl]-5,5-dimethyl-pyrazolidin-3-one (61 mg, 69% yield) was obtained as a light yellow solid, MS: m/e=311.2 (M+H⁺).

Step 5: 2-[5-(3-Fluoro-phenylethynyl)-pyrimidin-2-yl]-1,5,5-trimethyl-pyrazolidin-3-one

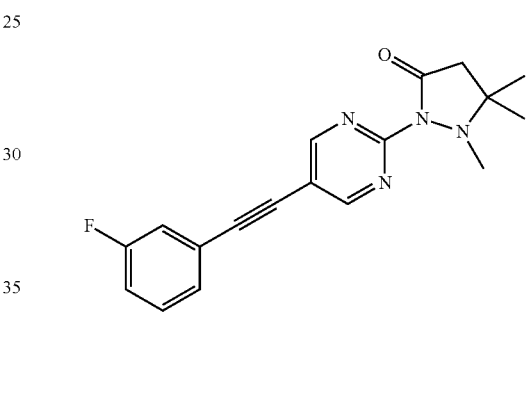

The title compound was obtained as a light brown solid, MS: m/e=325.3 (M+H⁺), using chemistry similar to that described in Example 3 from 2-[5-(3-fluoro-phenylethynyl)-pyrimidin-2-yl]-5,5-dimethyl-pyrazolidin-3-one (Example 15, step 4) and iodomethane.

Example 16

2-[5-(4-Fluoro-phenylethynyl)-pyrimidin-2-yl]-1,5,5-trimethyl-pyrazolidin-3-one

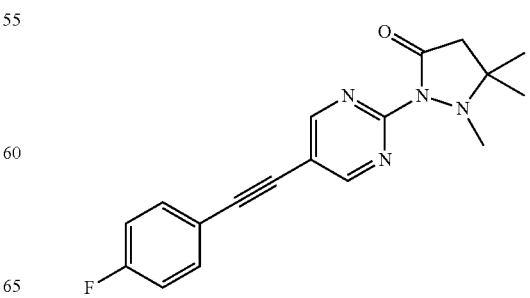

Step 1: 2-[5-(4-Fluoro-phenylethynyl)-pyrimidin-2-yl]-5,5-dimethyl-3-oxo-pyrazolidine-1-carboxylic acid tert-butyl ester

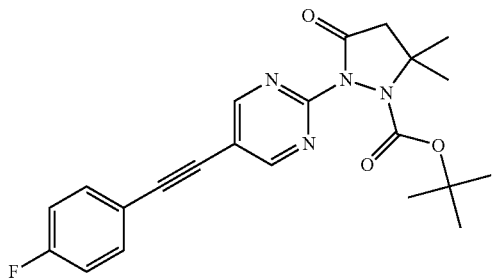 [SMILES: CC(C)(C)OC(=O)N1N(c2ncc(C#Cc3ccc(F)cc3)cn2)C(=O)CC1(C)C]

The title compound was obtained as an orange solid, MS: m/e=411.2 (M+H$^+$), using chemistry similar to that described in Example 1, step 3 from 2-(5-bromo-pyrimidin-2-yl)-5,5-dimethyl-3-oxo-pyrazolidine-1-carboxylic acid tert-butyl ester (Example 15, step 2) and 4-fluorophenylacetylene.

Step 2: 2-[5-(4-Fluoro-phenylethynyl)-pyrimidin-2-yl]-5,5-dimethyl-pyrazolidin-3-one

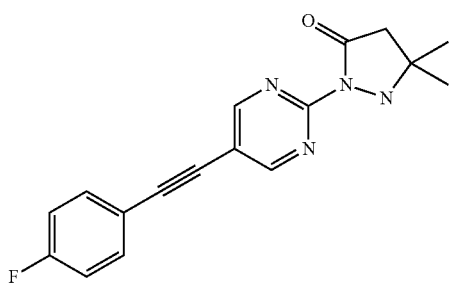

The title compound was obtained as a light yellow solid, MS: m/e=311.2 (M+H$^+$), using chemistry similar to that described in Example 15, step 4 from 2-[5-(4-fluoro-phenylethynyl)-pyrimidin-2-yl]-5,5-dimethyl-3-oxo-pyrazolidine-1-carboxylic acid tert-butyl ester (Example 16, step 1).

Step 3: 2-[5-(4-Fluoro-phenylethynyl)-pyrimidin-2-yl]-1,5,5-trimethyl-pyrazolidin-3-one

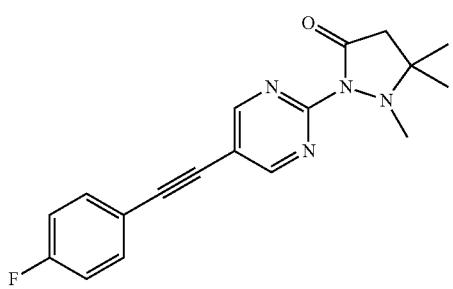 [SMILES: CN1N(c2ncc(C#Cc3ccc(F)cc3)cn2)C(=O)CC1(C)C]

The title compound was obtained as a light yellow solid, MS: m/e=325.3 (M+H$^+$), using chemistry similar to that described in Example 3 from 2-[5-(4-fluoro-phenylethynyl)-pyrimidin-2-yl]-5,5-dimethyl-pyrazolidin-3-one (Example 16, step 2) and iodomethane.

Example 17

2-[5-(2,5-Difluoro-phenylethynyl)-pyrimidin-2-yl]-1,5,5-trimethyl-pyrazolidin-3-one

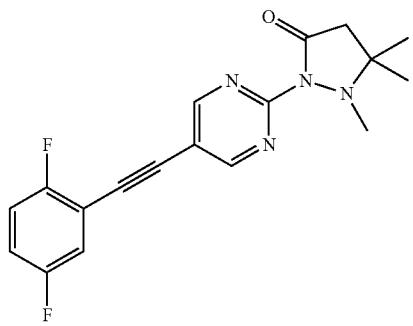 [SMILES: CN1N(c2ncc(C#Cc3cc(F)ccc3F)cn2)C(=O)CC1(C)C]

Step 1: 2-(5-Bromo-pyrimidin-2-yl)-5,5-dimethyl-pyrazolidin-3-one

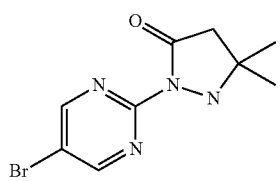

The title compound was obtained as a yellow solid, MS: m/e=271.1/273.1 (M+H$^+$), using chemistry similar to that described in Example 10, step 2 from 2-iodo-5-bromopyrimidine and 5,5-dimethyl-pyrazolidin-3-one (CAS 24572-33-6).

Step 2: 2-(5-Bromo-pyrimidin-2-yl)-1,5,5-trimethyl-pyrazolidin-3-one

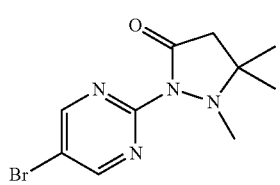 [SMILES: CN1N(c2ncc(Br)cn2)C(=O)CC1(C)C]

The title compound was obtained as a light yellow solid, MS: m/e=285.0/286.9 (M+H$^+$), using chemistry similar to that described in Example 3 from 2-(5-bromo-pyrimidin-2-yl)-5,5-dimethyl-pyrazolidin-3-one (Example 17, step 1) and iodomethane.

Step 3: 2-[5-(2,5-Difluoro-phenylethynyl)-pyrimidin-2-yl]-1,5,5-trimethyl-pyrazolidin-3-one

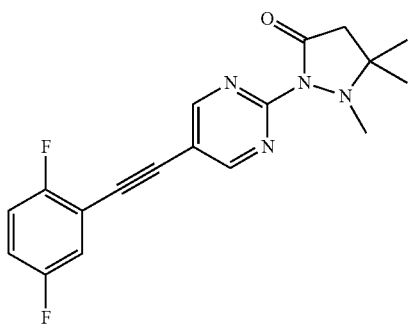 [SMILES: CN1N(c2ncc(C#Cc3cc(F)ccc3F)cn2)C(=O)CC1(C)C]

The title compound was obtained as a white solid, MS: m/e=343.3 (M+H⁺), using chemistry similar to that described in Example 1, step 3 from 2-(5-bromo-pyrimidin-2-yl)-1,5,5-trimethyl-pyrazolidin-3-one (Example 17, step 2) and 2,5-difluorophenylacetylene (CAS 956386-38-2).

Example 18

2-[5-(2-Chloro-pyridin-4-ylethynyl)-pyridin-2-yl]-1,5,5-trimethyl-pyrazolidin-3-one

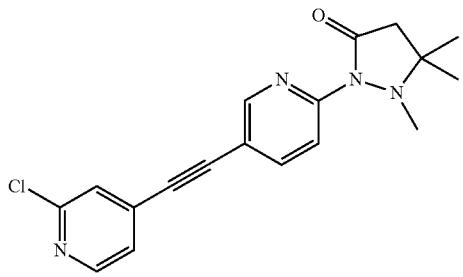 [SMILES: CN1N(c2ccc(C#Cc3ccnc(Cl)c3)cn2)C(=O)CC1(C)C]

Step 1: 2-Bromo-5-phenylethynyl-pyrimidine

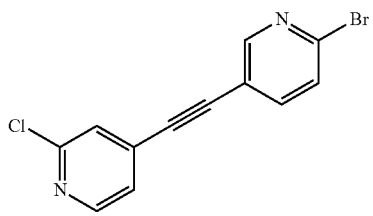 [SMILES: Clc1cc(C#Cc2ccc(Br)nc2)ccn1]

The title compound, a yellow solid, MS: m/e=293.2/295.2 (M+H⁺), can be obtained using chemistry similar to that described in Example 1, step 3 from 2-bromo-5-iodopyridine and 2-chloro-4-ethynyl-pyridine (CAS 945717-09-9).

Step 2: 2-[5-(2-Chloro-pyridin-4-ylethynyl)-pyridin-2-yl]-5,5-dimethyl-pyrazolidin-3-one

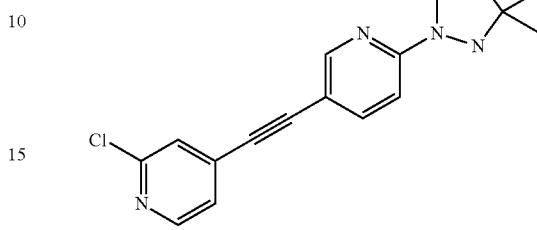

The title compound was obtained as a yellow solid, MS: m/e=327.4/329.4 (M+H⁺), using chemistry similar to that described in Example 10, step 2 from 2-bromo-5-phenylethynyl-pyrimidine (Example 18, step 1) and 5,5-dimethyl-pyrazolidin-3-one (CAS 24572-33-6).

Step 3: 2-[5-(2-Chloro-pyridin-4-ylethynyl)-pyridin-2-yl]-1,5,5-trimethyl-pyrazolidin-3-one

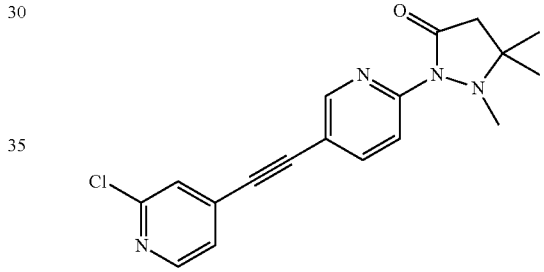

The title compound was obtained as a white solid, MS: m/e=341.4/343.3 (M+H⁺), using chemistry similar to that described in Example 3 from 2-[5-(2-chloro-pyridin-4-ylethynyl)-pyridin-2-yl]-5,5-dimethyl-pyrazolidin-3-one (Example 18, step 2) and iodomethane.

Example 19

2-[6-(2,5-Difluoro-phenylethynyl)-pyridazin-3-yl]-5,5-dimethyl-pyrazolidin-3-one

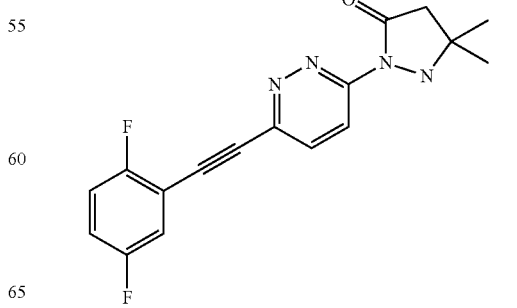

Step 1: 2-(6-Chloro-pyridazin-3-yl)-5,5-dimethyl-pyrazolidin-3-one

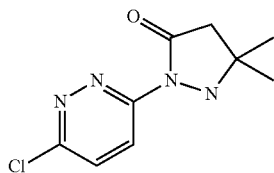

The title compound was obtained as a yellow oil, MS: m/e=227.1/229.3 (M+H⁺), using chemistry similar to that described in Example 1, step 2 from 1-benzotriazol-1-yl-3-methyl-but-2-en-1-one (Example 1, step 1) and (6-chloro-pyridazin-3-yl)-hydrazine (CAS 17284-97-8).

Step 2: 2-[6-(2,5-Difluoro-phenylethynyl)-pyridazin-3-yl]-5,5-dimethyl-pyrazolidin-3-one

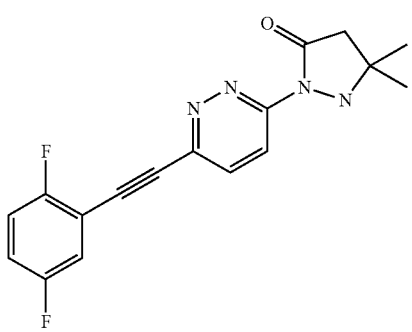 [SMILES: CC1(C)CC(=O)N(c2ccc(C#Cc3cc(F)ccc3F)nn2)N1]

The title compound was obtained as a light yellow solid, MS: m/e=329.2 (M+H⁺), using chemistry similar to that described in Example 1, step 3 from 2-(6-chloro-pyridazin-3-yl)-5,5-dimethyl-pyrazolidin-3-one (Example 19, step 1) and 2,5-difluorophenylacetylene (CAS 956386-38-2).

Example 20

2-[5-(2,5-Difluoro-phenylethynyl)-pyridin-2-yl]-5,5-dimethyl-pyrazolidin-3-one

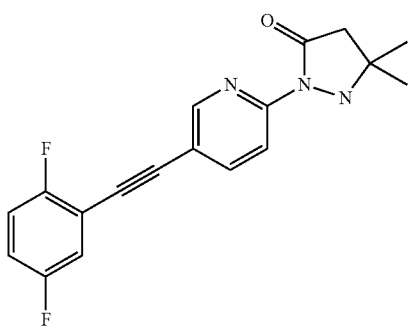 [SMILES: CC1(C)CC(=O)N(c2ccc(C#Cc3cc(F)ccc3F)cn2)N1]

The title compound, a brown oil, MS: m/e=328.1 (M+H⁺), can be obtained using chemistry similar to that described in Example 1, step 3 from 2-(5-bromo-pyridin-2-yl)-5,5-dimethyl-ethyl-pyrazolidin-3-one (Example 1, step 2) and 2,5-difluorophenylacetylene (CAS 956386-38-2).

Example 21

1-Ethyl-5,5-dimethyl-2-(5-phenylethynyl-pyridin-2-yl)-pyrazolidin-3-one

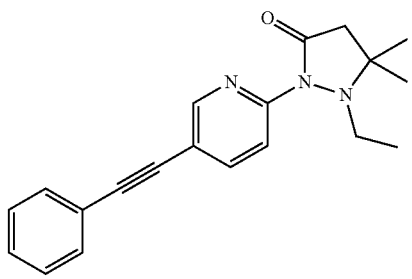 [SMILES: CCN1N(c2ccc(C#Cc3ccccc3)cn2)C(=O)CC1(C)C]

The title compound was obtained as a yellow oil, MS: m/e=320.4 (M+H⁺), using chemistry similar to that described in Example 10, step 2 from 2-bromo-5-phenylethynyl-pyridine (Example 10, step 1) and 1-ethyl-5,5-dimethyl-pyrazolidin-3-one (CAS 26485-97-2).

Example 22

1-Ethyl-2-[5-(4-fluoro-phenylethynyl)-pyridin-2-yl]-5,5-dimethyl-pyrazolidin-3-one

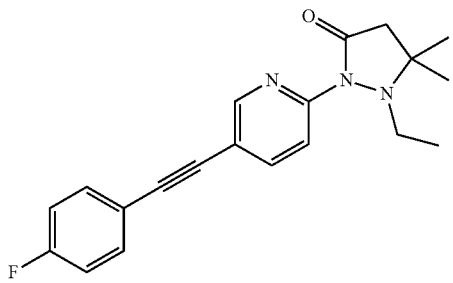 [SMILES: CCN1N(c2ccc(C#Cc3ccc(F)cc3)cn2)C(=O)CC1(C)C]

Step 1: 1-Ethyl-2-(5-iodo-pyridin-2-yl)-5,5-dimethyl-pyrazolidin-3-one

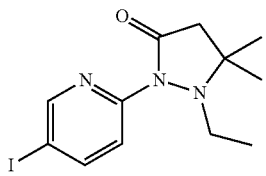 [SMILES: CCN1N(c2ccc(I)cn2)C(=O)CC1(C)C]

(200 mg, 0.90 mmol) 2-Fluoro-5-iodopyridine was dissolved in toluene (1 ml) and 1-ethyl-5,5-dimethyl-pyrazolidin-3-one [CAS 26485-97-2] (128 mg, 0.90 mmol, 1.0 equiv.) and cesium carbonate (440 mg, 1.35 mmol, 1.5 equiv.) were added under nitrogen. The mixture was stirred for 4 hours at 100° C. The crude product was purified by flash chromatography by directly loading the toluene mixture onto a silica gel column and eluting with an ethyl acetate:heptane gradient 0:100 to 50:50. The desired 1-ethyl-2-(5-iodo-pyridin-2-yl)-5,5-dimethyl-pyrazolidin-3-one (88 mg, 28% yield) was obtained as a yellow oil, MS: m/e=346.3 (M+H⁺).

Step 2: 1-Ethyl-2-[5-(4-fluoro-phenylethynyl)-pyridin-2-yl]-5,5-dimethyl-pyrazolidin-3-one

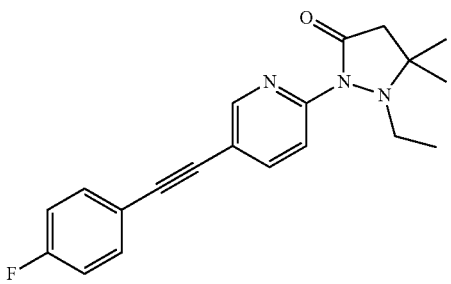 [SMILES: CCN1N(c2ccc(C#Cc3ccc(F)cc3)cn2)C(=O)CC1(C)C]

The title compound was obtained as a white solid, MS: m/e=338.4 (M+H⁺), using chemistry similar to that described in Example 1, step 3 from 1-ethyl-2-(5-iodo-pyridin-2-yl)-5,5-dimethyl-pyrazolidin-3-one (Example 22, step 1) and 4-fluorophenylacetylene.

Example 23

(RS)-1-Ethyl-5-isopropyl-2-(5-phenylethynyl-pyridin-2-yl)-pyrazolidin-3-one

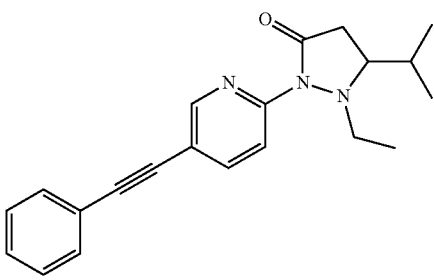 [SMILES: CCN1C(C(C)C)CC(=O)N1c1ccc(C#Cc2ccccc2)cn1]

The title compound was obtained as a light yellow oil, MS: m/e=334.4 (M+H⁺), using chemistry similar to that described in Example 10, step 2 from 2-bromo-5-phenylethynyl-pyridine (Example 10, step 1) and (RS)-1-ethyl-5-isopropyl-pyrazolidin-3-one (CAS 1185083-91-3).

Example 24

(RS)-5-Methyl-2-(5-phenylethynyl-pyridin-2-yl)-5-trifluoromethyl-pyrazolidin-3-one

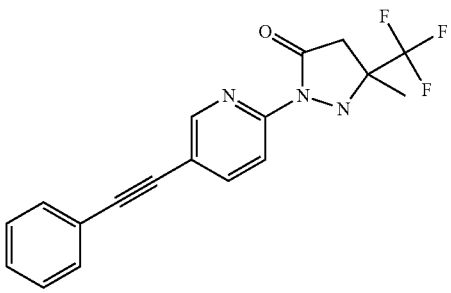 [SMILES: CC1(C(F)(F)F)CC(=O)N(c2ccc(C#Cc3ccccc3)cn2)N1]

Step 1: (RS)-5-Methyl-5-trifluoromethyl-pyrazolidin-3-one

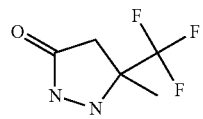

(300 mg, 1.65 mmol) 4,4,4-Trifluoro-3-methyl-but-2-enoic acid ethyl ester (CAS 24490-03-7) was dissolved in ethanol (3 ml) and hydrazine monohydrate 64% in ethanol (0.13 ml, 1.73 mmol, 1.05 equiv.) was added at room temperature and stirred in a sealed tube for 16 hours at 80° C. The reaction mixture was evaporated to dryness. The desired (RS)-5-methyl-5-trifluoromethyl-pyrazolidin-3-one (280 mg, quant.) was obtained as a white solid, MS: m/e=169.2 (M+H⁺).

Step 1: (RS)-5-Methyl-2-(5-phenylethynyl-pyridin-2-yl)-5-trifluoromethyl-pyrazolidin-3-one

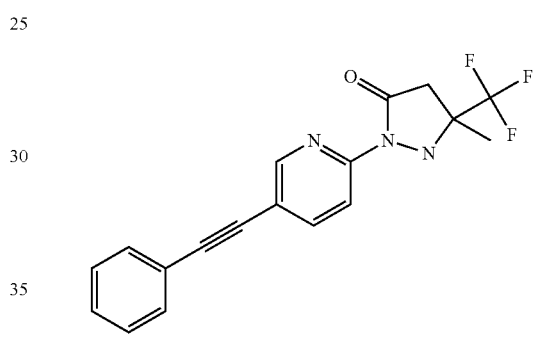

The title compound was obtained as a yellow oil, MS: m/e=346.4 (M+H⁺), using chemistry similar to that described in Example 10, step 2 from 2-bromo-5-phenylethynyl-pyridine (Example 10, step 1) and (RS)-5-methyl-5-trifluoromethyl-pyrazolidin-3-one (Example 24, step 1).

The invention claimed is:
1. A compound of formula I

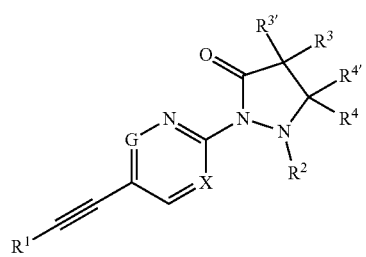

wherein
X is N or CH;
G is N or CH;
with the proviso that only one of X or G can be nitrogen;
$R^1$ is phenyl or pyridyl, each of which is optionally substituted by halogen, lower alkyl or lower alkoxy;
$R^2$ is hydrogen or lower alkyl or together with $R^4$ form a $C_3$-$C_6$-cycloalkyl;

R³, R³', R⁴ and R⁴' are each independently hydrogen, lower alkyl or CF₃;

or a pharmaceutically acceptable acid addition salt, racemate, enantiomer, optical isomer, or a stereoisomer thereof.

2. A compound having formula IA

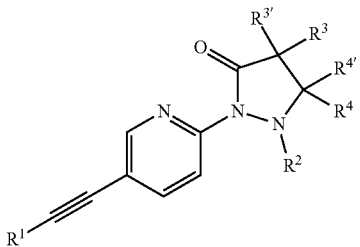

wherein

R¹ is phenyl or pyridyl, each of which is optionally substituted by halogen, lower alkyl or lower alkoxy;

R² is hydrogen or lower alkyl or together with R⁴ form a C₃-C₆-cycloalkyl;

R³, R³', R⁴ and R⁴' are each independently hydrogen, lower alkyl or CF₃;

or a pharmaceutically acceptable acid addition salt, racemate, enantiomer, optical isomer, or stereoisomer thereof.

3. The compound of claim 2, selected from the group consisting of 5,5-dimethyl-2-(5-phenylethynyl-pyridin-2-yl)-pyrazolidin-3-one;

(RS)-5-isopropyl-2-(5-phenylethynyl-pyridin-2-yl)-pyrazolidin-3-one;

1,5,5-trimethyl-2-(5-phenylethynyl-pyridin-2-yl)-pyrazolidin-3-one;

1,5,5-trimethyl-2-(5-m-tolylethynyl-pyridin-2-yl)-pyrazolidin-3-one;

2-[5-(3-fluoro-phenylethynyl)-pyridin-2-yl]-5,5-dimethyl-pyrazolidin-3-one;

2-[5-(3-fluoro-phenylethynyl)-pyridin-2-yl]-1,5,5-trimethyl-pyrazolidin-3-one;

2-[5-(3-chloro-phenylethynyl)-pyridin-2-yl]-1,5,5-trimethyl-pyrazolidin-3-one;

2-[5-(4-fluoro-phenylethynyl)-pyridin-2-yl]-5,5-dimethyl-pyrazolidin-3-one; and a pharmaceutically acceptable acid addition salt, racemate, enantiomer, optical isomer, or a stereoisomer thereof.

4. The compound of claim 2, selected from the group consisting of (RS)-1-(5-phenylethynyl-pyridin-2-yl)-tetrahydro-pyrrolo[1,2-b]pyrazol-2-one;

2-[5-(2-chloro-pyridin-4-ylethynyl)-pyridin-2-yl]-1,5,5-trimethyl-pyrazolidin-3-one;

2-[5-(2,5-difluoro-phenylethynyl)-pyridin-2-yl]-5,5-dimethyl-pyrazolidin-3-one;

1-ethyl-5,5-dimethyl-2-(5-phenylethynyl-pyridin-2-yl)-pyrazolidin-3-one;

1-ethyl-2-[5-(4-fluoro-phenylethynyl)-pyridin-2-yl]-5,5-dimethyl-pyrazolidin-3-one;

(RS)-1-ethyl-5-isopropyl-2-(5-phenylethynyl-pyridin-2-yl)-pyrazolidin-3-one;

(RS)-5-Methyl-2-(5-phenylethynyl-pyridin-2-yl)-5-trifluoromethyl-pyrazolidin-3-one;

and a pharmaceutically acceptable acid addition salt, racemate, enantiomer, optical isomer, or a stereoisomer thereof.

5. A compound having formula IB,

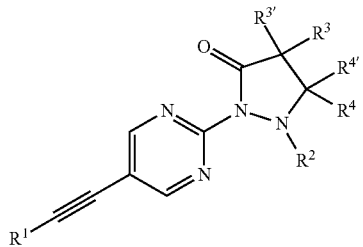

wherein

R¹ is phenyl or pyridyl, each of which is optionally substituted by halogen, lower alkyl or lower alkoxy;

R² is hydrogen or lower alkyl or together with R⁴ form a C₃-C₆-cycloalkyl;

R³, R³', R⁴ and R⁴' are each independently hydrogen, lower alkyl or CF₃;

or a pharmaceutically acceptable acid addition salt, racemate, enantiomer, optical isomer, or stereoisomer thereof.

6. The compound of claim 5, selected from the group consisting of 5,5-dimethyl-2-(5-phenylethynyl-pyrimidin-2-yl)-pyrazolidin-3-one;

(RS)-1-(5-phenylethynyl-pyrimidin-2-yl)-tetrahydro-pyrrolo[1,2-b]pyrazol-2-one;

(RS)-1-[5-(3-fluoro-phenylethynyl)-pyrimidin-2-yl]-tetrahydro-pyrrolo[1,2-b]pyrazol-2-one;

(RS)-1-[5-(4-fluoro-phenylethynyl)-pyrimidin-2-yl]-tetrahydro-pyrrolo[1,2-b]pyrazol-2-one;

1,5,5-trimethyl-2-(5-phenylethynyl-pyrimidin-2-yl)-pyrazolidin-3-one;

2-[5-(3-fluoro-phenylethynyl)-pyrimidin-2-yl]-1,5,5-trimethyl-pyrazolidin-3-one;

2-[5-(4-fluoro-phenylethynyl)-pyrimidin-2-yl]-1,5,5-trimethyl-pyrazolidin-3-one;

2-[5-(2,5-difluoro-phenylethynyl)-pyrimidin-2-yl]-1,5,5-trimethyl-pyrazolidin-3-one; and a pharmaceutically acceptable acid addition salt, racemate, enantiomer, optical isomer, or a stereoisomer thereof.

7. A compound having formula IC,

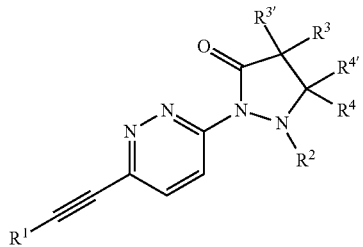

wherein

R¹ is phenyl or pyridyl, each of which is optionally substituted by halogen, lower alkyl or lower alkoxy;

R² is hydrogen or lower alkyl or together with R⁴ form a C₃-C₆-cycloalkyl;

$R^3$, $R^{3'}$, $R^4$ and $R^{4'}$ are each independently hydrogen, lower alkyl or $CF_3$;

or a pharmaceutically acceptable acid addition salt, racemate, enantiomer, optical isomer or stereoisomer thereof.

8. The compound of claim 7, wherein the compound is 2-[6-(2,5-difluoro-phenylethynyl)-pyridazin-3-yl]-5,5-dimethyl-pyrazolidin-3-one.

9. A pharmaceutical composition comprising a therapeutically effective amount of a compound of formula I

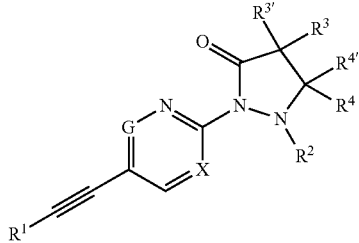

I wherein
X is N or CH;
G is N or CH;
with the proviso that only one of X or G can be nitrogen;
$R^1$ is phenyl or pyridyl, each of which is optionally substituted by halogen, lower alkyl or lower alkoxy;
$R^2$ is hydrogen or lower alkyl or together with $R^4$ form a $C_3$-$C_6$-cycloalkyl;
$R^3$, $R^{3'}$, $R^4$ and $R^{4'}$ are each independently hydrogen, lower alkyl or $CF_3$;
or a pharmaceutically acceptable acid addition salt, racemate, enantiomer optical isomer, or a stereoisomer thereof
and a pharmaceutically acceptable carrier.

10. A pharmaceutical composition comprising a therapeutically effective amount of a compound of formula IA

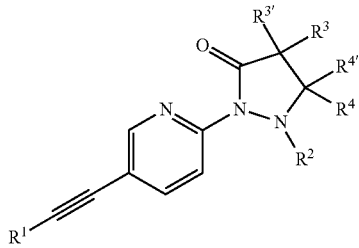

IA wherein
$R^1$ is phenyl or pyridyl, each of which is optionally substituted by halogen, lower alkyl or lower alkoxy;
$R^2$ is hydrogen or lower alkyl or together with $R^4$ form a $C_3$-$C_6$-cycloalkyl;
$R^3$, $R^{3'}$, $R^4$ and $R^{4'}$ are each independently hydrogen, lower alkyl or $CF_3$;

or a pharmaceutically acceptable acid addition salt, racemate, enantiomer, optical isomer, or stereoisomer thereof.

11. The pharmaceutical composition comprising a therapeutically effective amount of a compound of formula IB

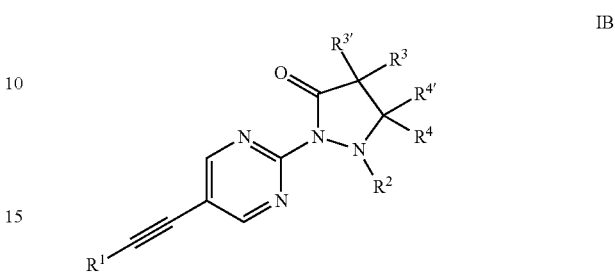

IB wherein
$R^1$ is phenyl or pyridyl, each of which is optionally substituted by halogen, lower alkyl or lower alkoxy;
$R^2$ is hydrogen or lower alkyl or together with $R^4$ form a $C_3$-$C_6$-cycloalkyl;
$R^3$, $R^{3'}$, $R^4$ and $R^{4'}$ are each independently hydrogen, lower alkyl or $CF_3$;
or a pharmaceutically acceptable acid addition salt, racemate, enantiomer, optical isomer, or stereoisomer thereof.

12. The pharmaceutical composition comprising a therapeutically effective amount of a compound of formula IC

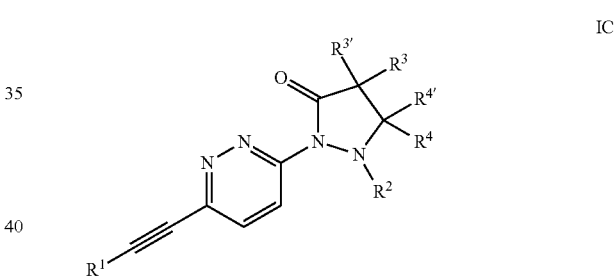

IC wherein
$R^1$ is phenyl or pyridyl, each of which is optionally substituted by halogen, lower alkyl or lower alkoxy;
$R^2$ is hydrogen or lower alkyl or together with $R^4$ form a $C_3$-$C_6$-cycloalkyl;
$R^3$, $R^{3'}$, $R^4$ and $R^{4'}$ are each independently hydrogen, lower alkyl or $CF_3$;
or a pharmaceutically acceptable acid addition salt, racemate, enantiomer, optical isomer or stereoisomer thereof.

13. The compound of claim 6 wherein said compound is 5,5-dimethyl-2-(5-phenylethynyl-pyrimidin-2-yl)-pyrazolidin-3-one;
or a pharmaceutically acceptable acid addition salt, racemate, enantiomer, optical isomer, or a stereoisomer thereof.

* * * * *